United States Patent
Beach et al.

(10) Patent No.: US 10,271,534 B2
(45) Date of Patent: Apr. 30, 2019

(54) SELECTIVE DETECTION OF BED BUGS PHEROMONES

(71) Applicant: DOW AGROSCIENCES LLC, Indianapolis, IN (US)

(72) Inventors: Mark W. Beach, Midland, MI (US); Andrey N. Soukhojak, Midland, MI (US); Neil A. Spomer, Carmel, IN (US); Shane L. Mangold, Midland, MI (US); Ravi B. Shankar, Midland, MI (US); Sukrit Mukhopadhyay, Midland, MI (US); Jeremy Chris P. Reyes, Lake Jackson, TX (US); Bruce A. Jacobs, Fishers, IN (US); William L. Winniford, Lake Jackson, TX (US); Ronda L. Hamm, Carmel, IN (US); Phillip J. Howard, Greenville, SC (US); Andrew J. Pasztor, Jr., Midland, MI (US); Mary D. Evenson, Zionsville, IN (US); Thomas G. Patterson, Westfield, IN (US); Natalie C. Giampietro, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/985,093

(22) Filed: May 21, 2018

(65) Prior Publication Data
US 2018/0332839 A1    Nov. 22, 2018

Related U.S. Application Data

(60) Provisional application No. 62/509,501, filed on May 22, 2017, provisional application No. 62/577,437, filed on Oct. 26, 2017.

(51) Int. Cl.
*A01M 1/02* (2006.01)

(52) U.S. Cl.
CPC ............ *A01M 1/026* (2013.01); *A01M 1/023* (2013.01); *A01M 2200/011* (2013.01)

(58) Field of Classification Search
USPC .................. 340/573.2; 43/114, 121, 123, 131
See application file for complete search history.

(56) References Cited

U.S. PATENT DOCUMENTS

8,026,822 B2    9/2011    Borth et al.
9,500,643 B2    11/2016   Vaidyanahan et al.
(Continued)

OTHER PUBLICATIONS

Vincent Harraca et al., "Nymphs of the common bed bug (*Cimex lectularius*) produce anti-aphrodisiac defence against conspecific males", BMC Biology, vol. 8:121, 2010, 7 pages.
(Continued)

*Primary Examiner* — Joseph H Feild
*Assistant Examiner* — Sharmin Akhter

(57) ABSTRACT

A device, system, and method of controlling pests are disclosed. A pest control device includes a sensor having a sensor cell and a controller. A surface of the sensor cell is coated with an agent that reacts with a targeted biochemical analyte secreted by pests. The controller is coupled to the sensor and is configured to receive sensor data from the sensor cell indicative of a rate of change in sensor mass detected on the surface of the sensor cell, determine whether the rate of change in the sensor mass based on the received sensor data exceeds a predefined threshold rate, and transmit a pest detection alert notification to a server in response to a determination that the rate of change exceeds the predetermined threshold rate.

17 Claims, 17 Drawing Sheets

(56) References Cited

U.S. PATENT DOCUMENTS

| 9,664,813 | B2 | 5/2017 | Janet et al. | |
|---|---|---|---|---|
| 2008/0148624 | A1* | 6/2008 | Borth | G01N 33/68 |
| | | | | 43/131 |
| 2017/0137501 | A1 | 5/2017 | Hall et al. | |
| 2017/0231211 | A1* | 8/2017 | Kupfer | A01M 1/08 |
| | | | | 43/113 |

OTHER PUBLICATIONS

Joelle F. Olson et al., "Two compounds in bed bug feces are sufficient to elicit off-host aggregation by bed bugs, *Cimex lectularius*", Pest Management Science, vol. 73, pp. 198-205, 2017, 8 pages.

Maria Rosa Ras et al., "Sampling and preconcentration techniques for determination of volatile organic compounds in air samples", Trends in Analytical Chemistry, vol. 28, No. 3, pp. 347-361, 2009, 15 pages.

Corraine A. McNeill et al., "Behavioral Responses of Nymph and Adult Cimex lectularius (Hemiptera: Cimicidae) to Colored Harborages", Journal of Medical Entomology, vol. 53(4), pp. 760-769, 2016, 10 pages.

\* cited by examiner

SELECTIVE DETECTION OF BED BUGS PHEROMONES

The present application claims the benefit of U.S. patent application Ser. No. 62/509,501, which was filed on May 22, 2017, and U.S. patent application Ser. No. 62/577,437, filed Oct. 26, 2017, which are expressly incorporated herein by reference.

TECHNICAL FIELD

The present disclosure relates generally to pest control, and more particularly, to the detection, monitoring, and control of insects, including for example, bed bugs.

BACKGROUND

Recent data suggests bed bug infestations (*Cimex* species) of human domiciles are on the rise. At least 92 species have been identified globally, of which at least 16 species are in the North American continent. Generally, bed bugs are parasitic pests with hosts including humans and various domesticated animals. It is believed that bed bug infestations are becoming more problematic now at least in part because long acting, residual insecticides are no longer being used to keep bed bug populations in check. In addition, increased international travel and insecticide resistance have made bed bug infestations spread and control with insecticides very difficult. In terms of scale, such infestations are of particular concern for hoteliers, cruise ships, trains, daycare facilities, and the like because of the business reputation risk posed by bad press or bad reviews. Other problematic areas tend to include nursing homes, barracks, dorms, hospitals, and various other forms of high density housing. Nonetheless, single family homes can likewise be impacted adversely.

An exemplary bed bug behavioral study is described in Corraine A. McNeill et al., *Journal Of Medical Entomology*, 2016 Jul. 1. 53(4):760-769, which is hereby incorporated by reference in its entirety. Exemplary studies about bed bug mating behavior and pheromone are described in Vincent Harraca et al., *BMC Biology*. 2010 Sep. 9; 8:121 and Joelle F Olson et al., *Pest Management Science*, 2017 January; 73(1): 198-205, each of which is hereby incorporated by reference in its entirety. Suitable sampling and pre-concentration techniques are described in Maria Rosa Ras et al., *Trac Trends In Analytical Chemistry*, 2009 Mar. 28(3): 347-361, which is hereby incorporated by reference in its entirety. Exemplary antibody detection methods for bed bugs are described in U.S. Pat. No. 9,500,643 and U.S. Pat. App. No. 2017/0137501, each of which is hereby incorporated by reference in its entirety. An exemplary detection system based on image analysis is described in U.S. Pat. No. 9,664,813, which is hereby incorporated by reference in its entirety.

SUMMARY

According to one aspect of the disclosure, a pest control device is disclosed. The pest control device comprises a sensor that includes a sensor cell and a controller coupled to the sensor. A surface of the sensor cell is coated with an agent that reacts with a targeted biochemical analyte secreted by pests. The controller is configured to receive sensor data from the sensor cell indicative of a rate of change in sensor mass detected on the surface of the sensor cell, determine whether the rate of change in the sensor mass based on the received sensor data exceeds a predefined threshold rate, and transmit a pest detection alert notification to a server in response to a determination that the rate of change exceeds the predetermined threshold rate. The rate of change correlates to an increase in the concentration of the targeted biochemical analyte.

In some embodiments, the pest control device may include a handle that provides a grip for a human operator to move the pest control device to identify a localized area of the targeted biochemical analyte.

In some embodiments, the controller may be further configured to activate a timer when the rate of change exceeds a predefined threshold rate, deactivate the timer when the rate of change returns to less than the predefined threshold rate, determine an amount of time that the rate of change in the sensor mass exceeded the predefined threshold rate, and determine whether the amount of time is greater than a predefined time period.

In some embodiments, the controller may transmit a pest detection alert notification in response to a determination that the amount of time is greater than the predefined time period.

In some embodiments, the predefined threshold rate may be a base mass change rate in the presence of bed bugs.

In some embodiments, the targeted biochemical analyte may include an analyte found in secretion of bed bugs. For example, in some embodiments, the targeted biochemical analyte may include trans-2-hexenal (T2H). Additionally or alternatively, in some embodiments, the targeted biochemical analyte may include trans-2-octenal (T2O). In some embodiments, the targeted biochemical analyte may include 4-oxo-(E)-2-hexenal. In some embodiments, the targeted biochemical analyte may include 4-oxo-(E)-2-octenal.

In some embodiments, the agent may include dioctyl cyclic thiol intermediate (dioctyl-CTI). Additionally or alternatively, in some embodiments, the agent may include cyclic thiol intermediate (CTI).

In some embodiments, the sensor may be a quartz crystal microbalance. In some embodiments, the sensor cell may be a quartz crystal resonator.

According to another aspect, a method of detecting a presence of pests is disclosed. The method includes receiving data indicative of a sensor mass rate of change from a sensor, determining whether the sensor mass rate of change exceeds a predefined threshold rate, and transmitting a pest detection alert notification to a server in response to a determination that the rate of change exceeds the predetermined threshold rate. The sensor includes a coating that reacts with a targeted biochemical analyte secreted by pests, and the sensor mass rate of change correlates to an increase in a concentration of a targeted biochemical analyte.

In some embodiments, the method may include activating a timer when the rate of change exceeds a predefined threshold rate, deactivating the timer when the rate of change returns to less than the predefined threshold rate, determining an amount of time that the rate of change in the sensor mass exceeded the predefined threshold rate, and determining whether the amount of time is greater than a predefined time period.

In some embodiments, transmitting the pest detection alert notification may include transmitting a pest detection alert notification in response to a determination that the amount of time is greater than the predefined time period.

In some embodiments, the predefined threshold rate may be a base mass change rate in the presence of bed bugs.

In some embodiments, the targeted biochemical analyte may include trans-2-hexenal (T2H). Additionally or alternatively, in some embodiments, the targeted biochemical analyte may include trans-2-octenal (T2O). In some embodiments, the targeted biochemical analyte may include 4-oxo-(E)-2-hexenal. In some embodiments, the targeted biochemical analyte may include 4-oxo-(E)-2-octenal.

In some embodiments, the coating may include dioctyl cyclic thiol intermediate (dioctyl-CTI). Additionally or alternatively, in some embodiments, the coating may include cyclic thiol intermediate (CTI).

In some embodiments, the sensor may be a quartz crystal microbalance.

In some embodiments, the surface of the sensor cell may be coated with a coating gel compound that includes a polymer gel and the agent.

In some embodiments, the polymer gel may have high viscosity and high thermal and chemical stability to form a stable coating on the surface of the sensor cell. In some embodiments, the polymer gel may have a low molecular weight.

In some embodiments, the polymer gel may be at least one of polymethylphenylsiloxiane (PMPS), polydimethylsiloxane (PDMS), fluoroalcohol polycarbosilane, fluoroalcohol polysiloxane, bisphenol-containing polymer (BSP3), poly-2-dimethylamin-ethyl-methacrylate (PDMAEMC), and polymers with silicone (Si) and iron (F).

In some embodiments, the polymer gel may be polymethylphenylsiloxiane (PMPS). Alternatively, in some embodiments, the polymer gel may be polydimethylsiloxane (PDMS). Alternatively, in some embodiments, the polymer gel may be fluoroalcohol polycarbosilane. Alternatively, in some embodiments, the polymer gel may be fluoroalcohol polysiloxane. Alternatively, in some embodiments, the polymer gel may be bisphenol-containing polymer (BSP3). Alternatively, in some embodiments, the polymer gel may be poly-2-dimethylamin-ethyl-methacrylate (PDMAEMC). Alternatively, in some embodiments, the polymer gel may be polymers with silicone (Si) and iron (F).

According to another aspect, a method of detecting a presence of pests is disclosed. The method includes receiving first sensor data from a sensor, receiving second sensor data from the sensor, determining a first slope of signal change based on the first and second sensor data, receiving third sensor data from the sensor, determining a second slope of signal change based on the second and third sensor data, determining if the second slope is different from the first slope, and transmitting a pest detection alert notification to a server in response to a determination that the second slope is different from the first slope. The sensor includes a coating that reacts with a targeted biochemical analyte secreted by pests, and the signal change correlates to an increase in a concentration of a targeted biochemical analyte.

In some embodiments, the method further includes activating a timer when the second slope is different from the first slope, receiving sensor data from the sensor and determining a slope of signal change based on the sensor data while the timer is active, deactivating the timer upon detecting no change in slope, determining a time interval measured by the timer, and determining whether the time interval is greater than a predefined time period. In some embodiments, transmitting the pest detection alert notification comprises transmitting a pest detection alert notification in response to a determination that the time interval is greater than the predefined time period.

In some embodiments, the predefined threshold rate may be a base mass change rate in the presence of bed bugs.

In some embodiments, the targeted biochemical analyte may include trans-2-hexenal (T2H). Additionally or alternatively, in some embodiments, the targeted biochemical analyte may include trans-2-octenal (T2O). In some embodiments, the targeted biochemical analyte may include 4-oxo-(E)-2-hexenal. In some embodiments, the targeted biochemical analyte may include 4-oxo-(E)-2-octenal.

In some embodiments, the coating may include dioctyl cyclic thiol intermediate (dioctyl-CTI). Additionally or alternatively, in some embodiments, the coating may include cyclic thiol intermediate (CTI).

In some embodiments, the sensor may be a quartz crystal microbalance.

In some embodiments, the coating includes a polymer gel and dioctyl cyclic thiol intermediate (dioctyl-CTI) or cyclic thiol intermediate (CTI).

In some embodiments, the polymer gel may have high viscosity and high thermal and chemical stability to form a stable coating on the surface of the sensor cell. In some embodiments, the polymer gel may have a low molecular weight.

In some embodiments, the polymer gel may be at least one of polymethylphenylsiloxiane (PMPS), polydimethylsiloxane (PDMS), fluoroalcohol polycarbosilane, fluoroalcohol polysiloxane, bisphenol-containing polymer (BSP3), poly-2-dimethylamin-ethyl-methacrylate (PDMAEMC), and polymers with silicone (Si) and iron (F).

In some embodiments, the polymer gel may be polymethylphenylsiloxiane (PMPS). Alternatively, in some embodiments, the polymer gel may be polydimethylsiloxane (PDMS). Alternatively, in some embodiments, the polymer gel may be fluoroalcohol polycarbosilane. Alternatively, in some embodiments, the polymer gel may be fluoroalcohol polysiloxane. Alternatively, in some embodiments, the polymer gel may be bisphenol-containing polymer (BSP3). Alternatively, in some embodiments, the polymer gel may be poly-2-dimethylamin-ethyl-methacrylate (PDMAEMC). Alternatively, in some embodiments, the polymer gel may be polymers with silicone (Si) and iron (F).

According to another aspect, a method includes determining an amount of agent available on a pest detection sensor to react with a targeted biochemical analyte secreted by pests, determining whether the amount of agent is below a threshold level, and transmitting a notification to a server indicating that the sensor requires a maintenance in response to a determination that the amount of agent is below the threshold level. An amount of the agent coated on the pest detection sensor decreases as the agent reacts with the targeted biochemical analyte.

In some embodiments, the agent may include dioctyl cyclic thiol intermediate (dioctyl-CTI). Additionally or alternatively, in some embodiments, the agent may include cyclic thiol intermediate (CTI).

In some embodiments, the targeted biochemical analyte may include an analyte found in secretion of bed bugs. For example, the targeted biochemical analyte may include trans-2-hexenal (T2H). Additionally or alternatively, in some embodiments, the targeted biochemical analyte may include trans-2-octenal (T2O). In some embodiments, the targeted biochemical analyte may include 4-oxo-(E)-2-hexenal. In some embodiments, the targeted biochemical analyte may include 4-oxo-(E)-2-octenal.

In some embodiments, the threshold level is determined based on a minimum amount of agent required to react with the targeted biochemical analyte.

According to another aspect, a cyclic thiol of the formula I

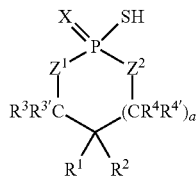

or a tautomer thereof is disclosed, wherein
X is S or O;
$Z^1$ and $Z^2$ are each independently O or S;
$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —(O$C_1$-$C_4$ alkylene)$_x$$R^5$, —(S$C_1$-$C_4$ alkylene)$_y$$R^5$, —(O$C_1$-$C_4$ alkylene)$_x$(S$C_1$-$C_4$ alkylene)$_y$$R^5$, —(S$C_1$-$C_4$ alkylene)$_y$(O$C_1$-$C_4$ alkylene)$_x$$R^5$, $C_1$-$C_3$ alkylene(O$C_1$-$C_4$ alkylene)$_x$$R^5$, $C_1$-$C_3$ alkylene(S$C_1$-$C_4$ alkylene)$_y$$R^5$, $C_1$-$C_3$ alkylene(O$C_1$-$C_4$ alkylene)$_x$(S$C_1$-$C_4$ alkylene)$_y$$R^5$, and $C_1$-$C_3$ alkylene(S$C_1$-$C_4$ alkylene)$_y$(O$C_1$-$C_4$ alkylene)$_x$$R^5$;
$R^2$ is selected from the group consisting of hydrogen, $C_3$-$C_{12}$ alkyl, $C_2$-$C_{12}$ alkenyl, $C_6$-$C_{10}$ aryl, 5- to 7-membered heteroaryl, —$OR^5$, —$SR^5$, —(O$C_1$-$C_4$ alkylene)$_x$$R^5$, —(S$C_1$-$C_4$ alkylene)$_y$$R^5$, —(O$C_1$-$C_4$ alkylene)$_x$(S$C_1$-$C_4$ alkylene)$_y$$R^5$, —(S$C_1$-$C_4$ alkylene)$_y$(O$C_1$-$C_4$ alkylene)$_x$$R^5$, $C_1$-$C_3$ alkylene(O$C_1$-$C_4$ alkylene)$_x$$R^5$, $C_1$-$C_3$ alkylene(S$C_1$-$C_4$ alkylene)$_y$$R^5$, $C_1$-$C_3$ alkylene(O$C_1$-$C_4$ alkylene)$_x$(S$C_1$-$C_4$ alkylene)$_y$$R^5$, and $C_1$-$C_3$ alkylene(S$C_1$-$C_4$ alkylene)$_y$(O$C_1$-$C_4$ alkylene)$_x$$R^5$;
$R^3$, $R^{3'}$, $R^4$, and $R^{4'}$ are each independently selected from the group consisting of hydrogen, $C_1$-$C_8$ alkyl, $C_2$-$C_8$ alkenyl, and $C_6$-$C_{10}$ aryl;
$R^5$ is selected from the group consisting of hydrogen, $C_1$-$C_8$ alkyl, $C_2$-$C_8$ alkenyl, $C_6$-$C_{10}$ aryl, and a polymeric bulking group;
a is 0 or 1; and
x and y are each independently an integer from 1 to 10.
In some embodiments, X may be S. In some embodiments, $Z^1$ may be O. In some embodiments, $Z^1$ and $Z^2$ may each be O. In some embodiments, X may be S, and $Z^1$ and $Z^2$ may each be O.
In some embodiments, $R^1$ and $R^2$ may each be $C_4$-$C_{10}$ alkyl and may be the same. For example, in some embodiments, $R^1$ and $R^2$ may each be octyl.
Additionally or alternatively, in some embodiments, at least one of $R^1$ and $R^2$ may be coupled to the polymeric bulking group. In some embodiments, at least one of $R^1$ and $R^2$ may be hydrogen.
In some embodiments, the polymeric bulking group may be selected from the group consisting of a silicone, a polyolefin, a polyamide, a polyester, a polycarbonate, a polyaramide, a polyurethane, a polystyrene, an epoxy, a rubber, a starch, a protein, a cellulose, an acrylate, an ABS polymer, a PEEK polymer, a polyol, polyether, polyetherpolyol, and a copolymer of two or more of the foregoing. For example, in some embodiments, the polymeric bulking group may be a silsesquioxane. In some embodiments, the polymeric bulking group may be crosslinked.
In some embodiments, $R^1$ may be of the formula $CH_2O(CH_2)_3S(CH_2)_3R^5$.
In some embodiments, the cyclic thiol may have a weight of about 350 Da to about 5000 Da.

In some embodiments, a may be 1.
In some embodiments, $R^3$, $R^{3'}$, $R^4$, and $R^{4'}$ may each be hydrogen.
In some embodiments, the cyclic thiol may be of the formula

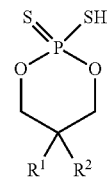

wherein $R^1$ and $R^2$ may each independently be hexyl or octyl. For example, in some embodiments, $R^1$ and $R^2$ may each be octyl.
In some embodiments, the thiol group may have a pKa of about 1 to about 4.
According to another aspect, a cyclic adduct of the formula II

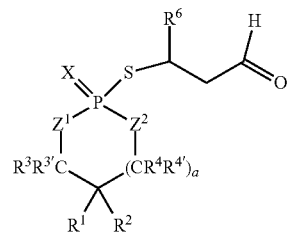

or a tautomer thereof is disclosed, wherein
X is S or O;
$Z^1$ and $Z^2$ are each independently O or S;
$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —(O$C_1$-$C_4$ alkylene)$_x$$R^5$, —(S$C_1$-$C_4$ alkylene)$_y$$R^5$, —(O$C_1$-$C_4$ alkylene)$_x$(S$C_1$-$C_4$ alkylene)$_y$$R^5$, —(S$C_1$-$C_4$ alkylene)$_y$(O$C_1$-$C_4$ alkylene)$_x$$R^5$, $C_1$-$C_3$ alkylene(O$C_1$-$C_4$ alkylene)$_x$$R^5$, $C_1$-$C_3$ alkylene(S$C_1$-$C_4$ alkylene)$_y$$R^5$, $C_1$-$C_3$ alkylene(O$C_1$-$C_4$ alkylene)$_x$(S$C_1$-$C_4$ alkylene)$_y$$R^5$, and $C_1$-$C_3$ alkylene(S$C_1$-$C_4$ alkylene)$_y$(O$C_1$-$C_4$ alkylene)$_x$$R^5$;
$R^2$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —(O$C_1$-$C_4$ alkylene)$_x$$R^5$, —(S$C_1$-$C_4$ alkylene)$_y$$R^5$, —(O$C_1$-$C_4$ alkylene)$_x$(S$C_1$-$C_4$ alkylene)$_y$$R^5$, —(S$C_1$-$C_4$ alkylene)$_y$(O$C_1$-$C_4$ alkylene)$_x$$R^5$, $C_1$-$C_3$ alkylene(O$C_1$-$C_4$ alkylene)$_x$$R^5$, $C_1$-$C_3$ alkylene(S$C_1$-$C_4$ alkylene)$_y$$R^5$, $C_1$-$C_3$ alkylene(O$C_1$-$C_4$ alkylene)$_x$(S$C_1$-$C_4$ alkylene)$_y$$R^5$, and $C_1$-$C_3$ alkylene(S$C_1$-$C_4$ alkylene)$_y$(O$C_1$-$C_4$ alkylene)$_x$$R^5$;
$R^3$, $R^{3'}$, $R^4$, and $R^{4'}$ are each independently selected from the group consisting of hydrogen, $C_1$-$C_8$ alkyl, $C_2$-$C_8$ alkenyl, and $C_6$-$C_{10}$ aryl;
$R^5$ is selected from the group consisting of hydrogen, $C_1$-$C_8$ alkyl, $C_2$-$C_8$ alkenyl, $C_6$-$C_{10}$ aryl, and a polymeric bulking group;
$R^6$ is $C_1$-$C_{12}$ alkyl or oxo substituted $C_1$-$C_{12}$ alkyl;
a is 0 or 1; and
x and y are each independently an integer from 1 to 10.
In some embodiments, $R^6$ may be propyl or pentyl. For example, in some embodiments, $R^6$ may be pentyl. In some embodiments, $R^6$ may be 1-oxopropyl or 1-oxopentyl.

According to another aspect, a thiol of the formula III

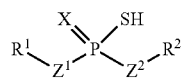

or a tautomer thereof is disclosed, wherein

X is S or O;

$Z^1$ and $Z^2$ are each independently O or S;

$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_x R^5$, —$(SC_1$-$C_4$ alkylene$)_y R^5$, —$(OC_1$-$C_4$ alkylene$)_x(SC_1$-$C_4$ alkylene$)_y R^5$, —$(SC_1$-$C_4$ alkylene$)_y(OC_1$-$C_4$ alkylene$)_x R^5$, $C_1$-$C_3$ alkylene$(OC_1$-$C_4$ alkylene$)_x R^5$, $C_1$-$C_3$ alkylene$(SC_1$-$C_4$ alkylene$)_y R^5$, $C_1$-$C_3$ alkylene$(OC_1$-$C_4$ alkylene$)_x(SC_1$-$C_4$ alkylene$)_y R^5$, and $C_1$-$C_3$ alkylene$(SC_1$-$C_4$ alkylene$)_y(OC_1$-$C_4$ alkylene$)_x R^5$;

$R^2$ is selected from the group consisting of $C_3$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_x R^5$, —$(SC_1$-$C_4$ alkylene$)_y R^5$, —$(OC_1$-$C_4$ alkylene$)_x(SC_1$-$C_4$ alkylene$)_y R^5$, —$(SC_1$-$C_4$ alkylene$)_y(OC_1$-$C_4$ alkylene$)_x R^5$, $C_1$-$C_3$ alkylene$(OC_1$-$C_4$ alkylene$)_x R^5$, $C_1$-$C_3$ alkylene$(SC_1$-$C_4$ alkylene$)_y R^5$, $C_1$-$C_3$ alkylene$(OC_1$-$C_4$ alkylene$)_x(SC_1$-$C_4$ alkylene$)_y R^5$, and $C_1$-$C_3$ alkylene$(SC_1$-$C_4$ alkylene$)_y(OC_1$-$C_4$ alkylene$)_x R^5$;

$R^5$ is selected from the group consisting of hydrogen, $C_1$-$C_8$ alkyl, $C_2$-$C_8$ alkenyl, $C_6$-$C_{10}$ aryl, and a polymeric bulking group;

a is 0 or 1; and x and y are each independently an integer from 1 to 10.

According to another aspect, an adduct of the formula IV

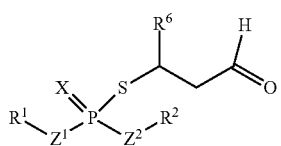

or a tautomer thereof is disclosed, wherein

X is S or O;

$Z^1$ and $Z^2$ are each independently O or S;

$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_x R^5$, —$(SC_1$-$C_4$ alkylene$)_y R^5$, —$(OC_1$-$C_4$ alkylene$)_x(SC_1$-$C_4$ alkylene$)_y R^5$, —$(SC_1$-$C_4$ alkylene$)_y(OC_1$-$C_4$ alkylene$)_x R^5$, $C_1$-$C_3$ alkylene$(OC_1$-$C_4$ alkylene$)_x R^5$, $C_1$-$C_3$ alkylene$(SC_1$-$C_4$ alkylene$)_y R^5$, $C_1$-$C_3$ alkylene$(OC_1$-$C_4$ alkylene$)_x(SC_1$-$C_4$ alkylene$)_y R^5$, and $C_1$-$C_3$ alkylene$(SC_1$-$C_4$ alkylene$)_y(OC_1$-$C_4$ alkylene$)_x R^5$;

$R^2$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_x R^5$, —$(SC_1$-$C_4$ alkylene$)_y R^5$, —$(OC_1$-$C_4$ alkylene$)_x(SC_1$-$C_4$ alkylene$)_y R^5$, —$(SC_1$-$C_4$ alkylene$)_y(OC_1$-$C_4$ alkylene$)_x R^5$, $C_1$-$C_3$ alkylene$(OC_1$-$C_4$ alkylene$)_x R^5$, $C_1$-$C_3$ alkylene$(SC_1$-$C_4$ alkylene$)_y R^5$, $C_1$-$C_3$ alkylene$(OC_1$-$C_4$ alkylene$)_x(SC_1$-$C_4$ alkylene$)_y R^5$, and $C_1$-$C_3$ alkylene$(SC_1$-$C_4$ alkylene$)_y(OC_1$-$C_4$ alkylene$)_x R^5$;

$R^5$ is selected from the group consisting of hydrogen, $C_1$-$C_8$ alkyl, $C_2$-$C_8$ alkenyl, $C_6$-$C_{10}$ aryl, and a polymeric bulking group;

$R^6$ is $C_1$-$C_{12}$ alkyl or oxo substituted $C_1$-$C_{12}$ alkyl;

a is 0 or 1; and x and y are each independently an integer from 1 to 10.

According to another aspect, a pest control device includes a housing including an inner chamber, a plurality of inlets opening into the inner chamber, and a plurality of inner walls dividing the inner chamber into a plurality of channels. Each channel is sized to receive one or more pests. The pest control device includes any sensor shown and/or described in this application and any controller shown and/or described in this application. The sensor is attached to the housing.

In some embodiments, the pest control device may further include an airflow device configured to produce an airflow to draw air along the plurality of channels from the inner chamber to the sensor.

In some embodiments, the housing may include a first panel moveable relative to a second panel to permit access to the inner chamber.

In some embodiments, the first panel may be pivotally coupled to the second panel.

In some embodiments, the housing may include an impermeable liner between an outer frame of the first panel and an outer frame of a second panel to minimize a loss of a targeted biochemical analyte through a gap between the outer frames.

In some embodiments, the impermeable liner may be an aluminized film.

In some embodiments, the first panel may include a base surface and the plurality of inner walls extend from the base surface.

In some embodiments, the first panel may include a ramp surface positioned outside of each inlet to guide pests into the corresponding inlet.

In some embodiments, the plurality of inner walls may include a pair of guide walls positioned on each side of an inlet and a barrier wall. Each guide wall may extend in a first direction and define a first channel of the plurality of channels. The barrier wall may be spaced apart from the ends of the guide walls and extend in a second direction orthogonal to the first direction.

In some embodiments, the barrier wall may include a first wall section extending in the second direction orthogonal to the first direction, a second wall section extending from an end of the first wall section, and a third wall section extending from an opposite end of the first wall section. The second wall section may extend parallel to the guide walls and cooperate to define a second channel of the plurality of channels. The second wall section may extend parallel to the guide walls and cooperate to define a third channel of the plurality of channels.

In some embodiments, the first channel may be configured to direct the airflow in the first direction, and the second and third channels may be configured to direct the airflow in a third direction opposite the first direction.

In some embodiments, the barrier wall may be a first barrier wall, and the plurality of inner walls may include a second barrier wall spaced apart from the end of the first barrier wall. The first barrier wall and the second barrier wall may cooperate to define a fourth channel configured to direct airflow in the first direction.

In some embodiments, the fourth channel may be offset from the inlets of housing.

In some embodiments, the sensor may be positioned in the inner chamber of the housing.

In some embodiments, the airflow device may be positioned in the inner chamber.

In some embodiments, the pest control device may further include an external pre-concentrator.

In some embodiments, the pre-concentrator may include a heating element to increase temperature in the inner chamber.

In some embodiments, the pre-concentrator may include a sheet that sorbs a targeted biochemical analyte.

In some embodiments, the sheet may be made of a woven or non-woven fibrous material and include sorbent powder between fibers of a sheet of fibrous material.

In some embodiments, the pre-concentrator may include multiple sheets made of a woven or non-woven fibrous material that sorb a targeted biochemical analyte and include sorbent powder between two sheets of a fibrous material.

In some embodiments, the pre-concentrator may include a tube that extends from an inlet of the plurality of inlets to the sensor and sorbs a targeted biochemical analyte.

In some embodiments, the pre-concentrator may include a test chamber sized to receive an amount of a targeted biochemical analyte.

In some embodiments, the pre-concentrator may include a surface configured to sorb a targeted biochemical analyte at a first temperature and release the targeted biochemical analyte at a second temperature.

In some embodiments, the pest control device may further include a heating element operable to selectively adjust temperature in the inner chamber.

In some embodiments, the heating element may be operable increase the temperature to exterminate pests in the inner chamber.

In some embodiments, the housing may be configured to be secured to a bed.

In some embodiments, the pest control device may further include a headboard of a bed, and the housing is configured to be secured to the headboard of the bed.

BRIEF DESCRIPTION OF THE DRAWINGS

The detailed description particularly refers to the following figures, in which.

DETAILED DESCRIPTION OF THE DRAWINGS

Figure 1:
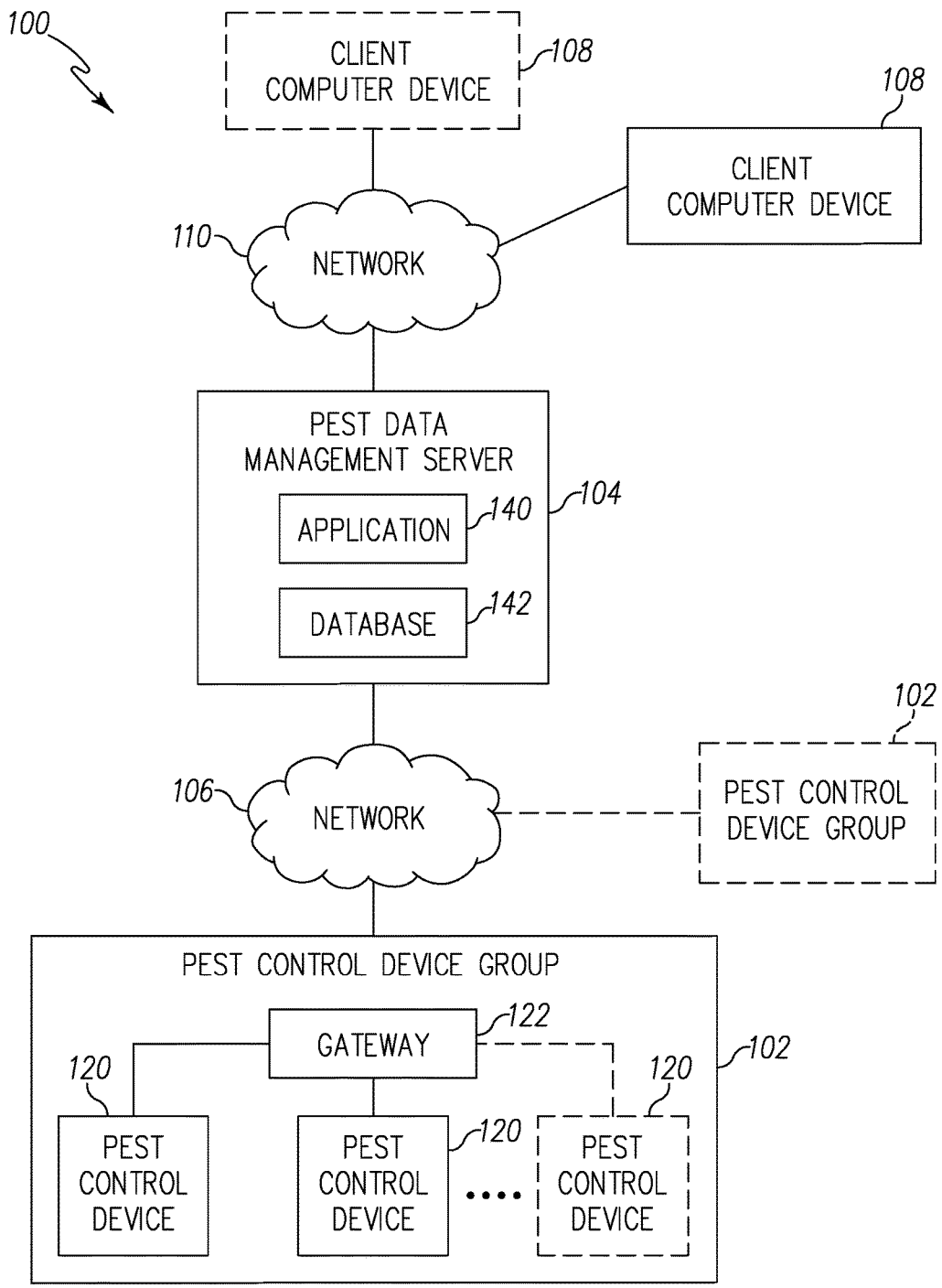
FIG. 1 is a diagrammatic view of at least one embodiment of a pest control system that includes a plurality of pest control devices.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a pest control system 100 for detecting a presence of pests is shown. The system 100 illustratively includes one or more pest control device groups 102 that communicate with a central pest data management server 104 via a network 106. The central pest data management server 104 is further configured to communicate with one or more client compute device 108 via a network 110 to transmit information received from the pest control device group 102.

The pest control device group 102 includes a plurality of pest control devices 108. Each pest control device 108 is configured to detect a presence of bed bugs and provides sensor data indicative of the detection of the bed bugs, as described in more detail below. The pest control device 108 transmits the sensor data to the central pest data management server 104 via the network 106. To do so, in the illustrative embodiment, the plurality of pest control devices 120 communicates with a gateway 122 to transmit sensor data to the network 106. It should be appreciated that in other embodiments or in other pest control groups 102, one or more of the control devices 120 may communicate directly with the network 106.

The gateway 122 may be embodied as any type of computation or computer device capable of wirelessly communicating with the pest control device 120 and the network 106. In some embodiments, a range extender or repeaters may be used to extend a range of communications between the pest control device 102 and the gateway 122. Additionally, the gateway 122 may incorporate a two-way transceiver for communicating with the pest control device 120 and/or repeaters and the network 106. In the illustrative embodiment, the gateway device may incorporate digital cellular technology to permit it to communicate with the network 106. An exemplary system of repeaters and gateway devices is shown and described in U.S. Pat. No. 8,026,822, which issued Sep. 8, 2009 and is expressly incorporated herein by reference.

The network 106 may be embodied as any type of network capable of facilitating communications between the gateway 122 of the pest control device group 120 and the central pest data management server 104. In the illustrative embodiment, the network 106 may be embodied as a cellular network or a wireless wide area network (WAN) using the cellular network. It should be appreciated that, in some embodiments, the network 106 may be embodied as, or otherwise include, a wireless local area network (LAN), a wide area network (WAN), and/or a publicly-accessible, global network such as the Internet. As such, the network 106 may include any number of additional devices, such as additional computers, routers, and switches, to facilitate communications thereacross. In other embodiments, each of the pest control sensor 120 may include a separate transmitter and receiver for transmitting and receiving data from the server 104 using the network 106. In still other embodiments, the gateway 122 may be configured to be hardwired to the network 106 via a cable.

The server 104 includes communications middleware, application software 140, and a database 142. It should be appreciated that the server 104 may be located on-site with the pest control device 120 or off site. The server 104 may be embodied as any type of computation or computer device capable of performing the functions described herein including, without limitation, a server, a computer, a multiprocessor system, a rack-mounted server, a blade server, a laptop computer, a notebook computer, a tablet computer, a wearable computing device, a network appliance, a web appliance, a distributed computing system, a processor-based system, and/or a consumer electronic device. It should be appreciated that the server 104 may be embodied as a single computing device or a collection of distributed computing devices. In the illustrative embodiment, the server 104 provides various virtual/logical components to allow sensor data of each of the pest control devices 120 received via the gateway 122 to be aggregated into database 142. It should be appreciated that the server 104 may communicate with all remote pest control device groups 102, evaluate resulting data, and take corresponding actions using an Application Service Provider (ASP) model. Among other things, the server 104 collects the sensor data from the pest control device group 102, aggregates and processes sensor data, and determines what information needs to be forwarded to a customer or technician. In addition, the server 104 facilitates a data archive, notification and reporting process.

The client compute device 108 may be embodied as any type of computation or computer device capable of communicating with the server 104 including, without limitation, a computer, a multiprocessor system, a laptop computer, a notebook computer, a tablet computer, a wearable computing device, a network appliance, a web appliance, a distributed computing system, a processor-based system, and/or a consumer electronic device. In the illustrative embodiment, the client compute device 108 may selectively access the server 104 through the network 110. The client compute device 108 may include browser subsystem, spreadsheet interface, email interface, Short Message Service (SMS) interface, and other interface subsystems.

The network 110 may be embodied as any type of network capable of facilitating communications between the client compute device 108 and the central pest data management server 104. In the illustrative embodiment, the network 110 may be embodied as a wireless local area network (LAN) or a publicly-accessible, global network such as the Internet. However, it should be appreciated that, in some embodiments, the network 110 may be embodied as, or otherwise include, a cellular network or a wireless wide area network (WAN). As such, the network 110 may include any number of additional devices, such as additional computers, routers, and switches, to facilitate communications thereacross.

Figure 2:
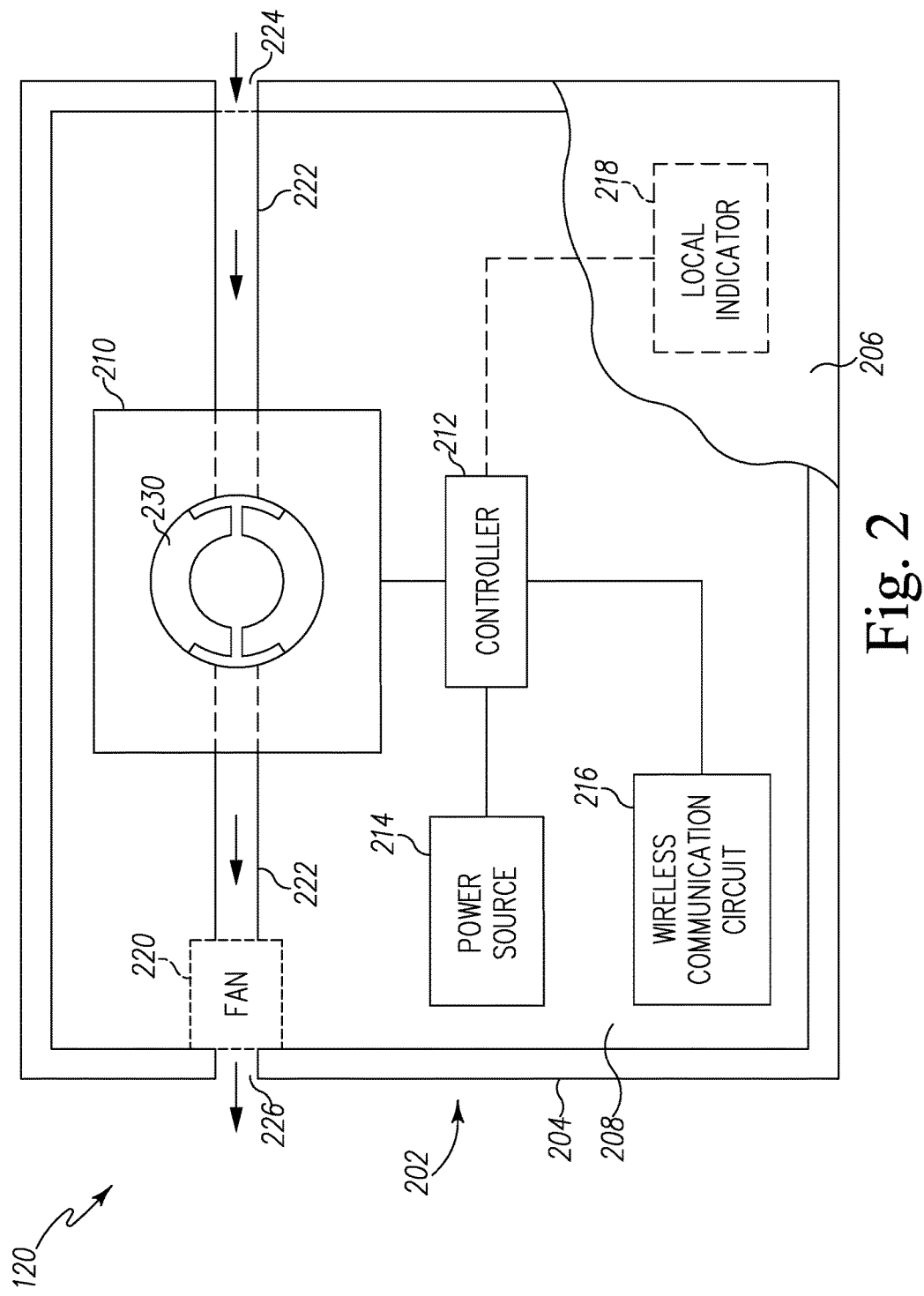
FIG. 2 is a diagrammatic view of at least one embodiment of a pest control device that can be included in the pest control system of FIG. 1.

Referring now to FIG. 2, a pest control device 120 for detecting a presence of pests is shown in greater detail. The pest control device 120 includes a housing 202 defined by an exterior wall 204 and a top cover 206 enclosing an internal chamber 208. In the illustrative embodiment, the internal chamber 208 houses a sensor 210, a controller 212, a power source 214, and a wireless communication circuit 216. In some embodiments, the internal chamber 208 may house a local indicator 218.

The sensor 210 is configured to detect a targeted biochemical analyte found in the secretion of pests. For example, in the illustrative embodiment, the sensor 210 is configured to detect a targeted biochemical analyte found in the secretion of bed bugs. The sensor 210 is coupled to a conduit 222 on each side of the sensor 210, which extends through the exterior wall 204 at an inlet 224 and an outlet 226. The secretion of bed bugs enters the inlet 224 and flows into the sensor 210 through the conduit 222. It should be appreciated that, in some embodiments, a fan 220 may be positioned in the internal chamber 208 near the outlet 226 in order to draw air from the inlet 224 towards the outlet 226 through the sensor 210.

The sensor 210 may be embodied as any type of device, circuit, or component capable of performing the functions described herein. In the illustrative embodiment, the sensor 210 is embodied as a resonator sensor such as a quartz crystal microbalance (QCM). As shown in FIG. 2, the sensor 210 includes a sensor cell or quartz crystal resonator 230 such that the conduit 222 extends into the quartz crystal resonator 230 to distribute air through the quartz crystal resonator 230. It should be appreciated that, in some embodiments, the sensor 210 may include a series of multiple sensor cells or quartz crystal resonators 230 that are arranged in parallel such that the conduit 222 is split into multiple lines into multiple quartz crystal resonators 230 to distribute air through each of the quartz crystal resonator 230.

In use, the power source 214 provides power to the sensor 210 to oscillate the quartz crystal resonator 230, and the quartz crystal resonator 230 is configured to measure a frequency of oscillation. The quartz crystal resonator 230 is further configured to generate sensor data that includes the frequency of the oscillating quartz crystal resonator 230, which is indicative of mass change on the surface of the quartz crystal resonator 230. It should be appreciated that the frequency of oscillation of quartz crystal resonator 230 is generally dependent on the sensor mass detected on the surface of the quartz crystal resonator 230. For example, the frequency of oscillation decreases as the mass deposited on the surface of the quartz crystal resonator 230 increases. As such, a mass variation per unit area may be determined based on the sensor data received from the quartz crystal resonator 230. Accordingly, the controller 212 of the pest control device 120 may further determine the change in sensor mass based on the change in frequency of oscillation. In some embodiments, the sensor 210 may be a small-scale QCM sensor, such as an openQCM. It should be appreciated that, in some embodiments, the sensor 210 may be any type of mass resonator that can detect the presence of the targeted biochemical analyte. In some embodiments, the sensor 210 may be embodied as a cantilever sensor. In other embodiments, the sensor 210 may be embodied as a cantilever sensor.

Figure 3:
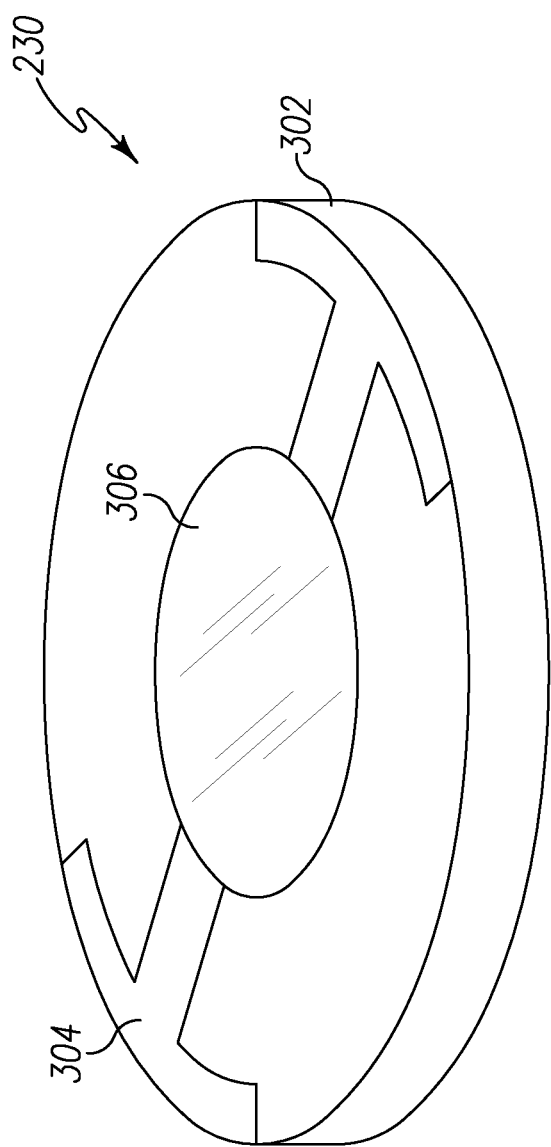
FIG. 3 is a perspective view of at least one embodiment of a detection sensor of a pest control device that can be included in the pest control device of FIG. 2.

As shown in FIG. 3, the quartz crystal resonator 230 is coated with a sensor coating 306 on the surface of the quartz crystal resonator 230. In the illustrative embodiment, the quartz crystal resonator 230 includes a quartz crystal 302 and an electrode 304. It should be appreciated that the sensor coating 306 may be deposited on an entire surface or a partial surface of the quartz crystal 302.

In the illustrative embodiment, the sensor coating 306 is made of an agent that reacts with the targeted biochemical analyte found in the secretion of bed bugs. In the illustrative embodiment, the targeted biochemical analyte is an unsaturated aldehyde compound, such as, for example, trans-2-hexenal (T2H), trans-2-octenal (T2O), 4-oxo-(E)-2-hexenal, and/or 4-oxo-(E)-2-octenal. In the illustrative embodiment, dioctyl-cyclic thiol intermediate (dioctyl-CTI) is used to form the sensor coating 306 because it selectively reacts with T2H, T2O, 4-oxo-(E)-2-hexenal, and/or 4-oxo-(E)-2-octenal. In the illustrative embodiment, the dioctyl-CTI has the formula

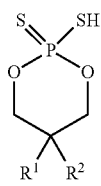

wherein $R^1$ and $R^2$ are each octyl. It should be appreciated that, in other embodiments, the agent may be cyclic thiol intermediate (CTI) or other CTI-functional group that reacts with the targeted biochemical analyte. When it reacts with T2H, T2O, 4-oxo-(E)-2-hexenal, and/or 4-oxo-(E)-2-octenal, dioctyl-CTI produces a product that has a higher molecular weight than the dioctyl-CTI alone. In the illustrative embodiment, the product has the formula

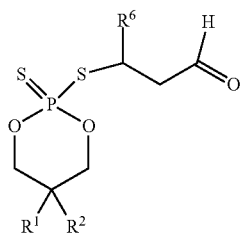

wherein $R^1$ and $R^2$ are each octyl and $R^6$ is pentyl. In some embodiments, dioctyl-CTI may be mixed with polymers to increase the viscosity of dioctyl-CTI to create a uniform film of the dioctyl-CTI on the quartz crystal resonator 230 and to prevent de-wetting of the dioctyl-CTI compounds on the quartz crystal resonator 230. It should be appreciated that the frequency of oscillation of the quartz crystal resonator 230 is partially dependent on the mass of the agent coated on the quartz crystal resonator 230.

In some embodiments, the agent of the sensor coating 306 is a cyclic thiol is of the formula I

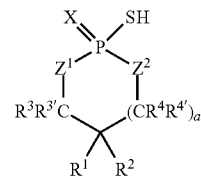

or a tautomer thereof, wherein

X is S or O;

$Z^1$ and $Z^2$ are each independently O or S;

$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_x R^5$, —$(SC_1$-$C_4$ alkylene$)_y R^5$, —$(OC_1$-$C_4$ alkylene$)_x (SC_1$-$C_4$ alkylene$)_y R^5$, —$(SC_1$-$C_4$ alkylene$)_y (OC_1$-$C_4$ alkylene$)_x R^5$, $C_1$-$C_3$ alkylene$(OC_1$-$C_4$ alkylene$)_x R^5$, $C_1$-$C_3$ alkylene$(SC_1$-$C_4$ alkylene$)_y R^5$, $C_1$-$C_3$ alkylene$(OC_1$-$C_4$ alkylene$)_x (SC_1$-$C_4$ alkylene$)_y R^5$, and $C_1$-$C_3$ alkylene$(SC_1$-$C_4$ alkylene$)_y (OC_1$-$C_4$ alkylene$)_x R^5$;

$R^2$ is selected from the group consisting of hydrogen, $C_3$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_x R^5$, —$(SC_1$-$C_4$ alkylene$)_y R^5$, —$(OC_1$-$C_4$ alkylene$)_x (SC_1$-$C_4$ alkylene$)_y R^5$, —$(SC_1$-$C_4$ alkylene$)_y (OC_1$-$C_4$ alkylene$)_x R^5$, $C_1$-$C_3$ alkylene$(OC_1$-$C_4$ alkylene$)_x R^5$, $C_1$-$C_3$ alkylene$(SC_1$-$C_4$ alkylene$)_y R^5$, $C_1$-$C_3$ alkylene$(OC_1$-$C_4$ alkylene$)_x (SC_1$-$C_4$ alkylene$)_y R^5$, and $C_1$-$C_3$ alkylene$(SC_1$-$C_4$ alkylene$)_y (OC_1$-$C_4$ alkylene$)_x R^5$;

$R^3$, $R^{3'}$, $R^4$, and $R^{4'}$ are each independently selected from the group consisting of hydrogen, $C_1$-$C_8$ alkyl, $C_2$-$C_8$ alkenyl, and $C_6$-$C_{10}$ aryl;

$R^5$ is selected from the group consisting of hydrogen, $C_1$-$C_8$ alkyl, $C_2$-$C_8$ alkenyl, $C_6$-$C_{10}$ aryl, and a polymeric bulking group;

a is 0 or 1; and x and y are each independently an integer from 1 to 10.

In some embodiments, X is S. In some embodiments, $Z^1$ is O. In some embodiments, $Z^2$ is O. In some embodiments, $Z^1$ and $Z^2$ are each O. In some embodiments, X is S, and $Z^1$ and $Z^2$ are each O.

In some embodiments, $R^1$ and $R^2$ are the same. In some embodiments, $R^1$ and $R^2$ are each independently $C_4$-$C_{10}$ alkyl. In some embodiments, $R^1$ and $R^2$ are each $C_4$-$C_{10}$ alkyl and are the same. In some embodiments, $R^1$ and $R^2$ are each independently $C_6$-$C_8$ alkyl. In some embodiments, $R^1$ and $R^2$ are each $C_6$-$C_8$ alkyl and are the same. In some embodiments, $R^1$ and $R^2$ are each octyl.

In some embodiments, at least one of $R^1$ and $R^2$ is coupled to the polymeric bulking group. In some embodiments, at least one of $R^1$ and $R^2$ is hydrogen.

In some embodiments, the polymeric bulking group is selected from the group consisting of a silicone, a polyolefin, a polyamide, a polyester, a polycarbonate, a polyaramide, a polyurethane, a polystyrene, an epoxy, a rubber, a starch, a protein, a cellulose, an acrylate, an ABS polymer, a PEEK polymer, a polyol, polyether, polyetherpolyol, and a copolymer of two or more of the foregoing. In some embodiments, the polymeric bulking group is a silicone. In some embodiments, the polymeric bulking group is a silsesquioxane. In some embodiments, the polymeric bulking group is crosslinked.

As used herein, "polymeric bulking group" refers to oligomers and polymers, which in some embodiments are silsesquioxanes. Examples of silsesquioxane compounds are described in Cordes, D., et al., *Chem. Rev.* 2010, 11, 2081-2173, expressly incorporated herein by reference.

In some embodiments, $R^1$ is —$(OC_1$-$C_4$ alkyl$)_xR^5$ or $C_1$-$C_3$ alkyl$(OC_1$-$C_4$ alkyl$)_xR^5$. In some embodiments, $R^1$ comprises —$(OC_1$-$C_4$ alkyl$)_x(SC_1$-$C_4$ alkyl$)_yR^5$ or $C_1$-$C_3$ alkyl$(OC_1$-$C_4$ alkyl$)_x(SC_1$-$C_4$ alkyl$)_yR^5$. In some embodiments, $R^1$ is of the formula —$CH_2O(CH_2)_3S(CH_2)_3R^5$.

In some embodiments, the cyclic thiol has a weight of about 200 Da to about 5000 Da. In some embodiments, the cyclic thiol has a weight of about 350 Da to about 5000 Da. In some embodiments, the cyclic thiol has a weight of about 1000 Da to about 5000 Da.

In some embodiments, a is 1.

In some embodiments, $R^3$, $R^{3'}$, $R^4$, and $R^{4'}$ are each hydrogen.

In some embodiments, the cyclic thiol is of the formula

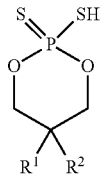

wherein $R^1$ and $R^2$ are each independently hexyl or octyl.

In some embodiments, the thiol group has a pKa of about 1 to about 4. In some embodiments, the thiol group has a pKa of about 2.5.

In some embodiments, the cyclic thiol is part of a composition that is free of metal thiol chelators. In some embodiments, the composition has a pH of about 2 to about 8. In some embodiments, the composition has a pH of about 2 to about 9. In some embodiments, the composition has a pH of about 7.

In some embodiments, when the agent of the sensor coating 306 reacts with the targeted biochemical analyte, a cyclic adduct is formed. In some embodiments, the cyclic adduct is of the formula II

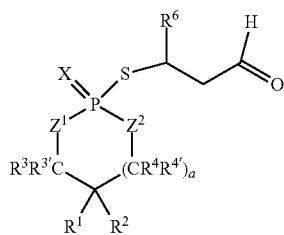

or a tautomer thereof, wherein

X is S or O;

$Z^1$ and $Z^2$ are each independently O or S;

$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_xR^5$, —$(SC_1$-$C_4$ alkylene$)_yR^5$, —$(OC_1$-$C_4$ alkylene$)_x(SC_1$-$C_4$ alkylene$)_yR^5$, —$(SC_1$-$C_4$ alkylene$)_y(OC_1$-$C_4$ alkylene$)_xR^5$, $C_1$-$C_3$ alkylene$(OC_1$-$C_4$ alkylene$)_xR^5$, $C_1$-$C_3$ alkylene$(SC_1$-$C_4$ alkylene$)_yR^5$, $C_1$-$C_3$ alkylene$(OC_1$-$C_4$ alkylene$)_x(SC_1$-$C_4$ alkylene$)_yR^5$, and $C_1$-$C_3$ alkylene$(SC_1$-$C_4$ alkylene$)_y(OC_1$-$C_4$ alkylene$)_xR^5$;

$R^2$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_xR^5$, —$(SC_1$-$C_4$ alkylene$)_yR^5$, —$(OC_1$-$C_4$ alkylene$)_x(SC_1$-$C_4$ alkylene$)_yR^5$, —$(SC_1$-$C_4$ alkylene$)_y(OC_1$-$C_4$ alkylene$)_xR^5$, $C_1$-$C_3$ alkylene$(OC_1$-$C_4$ alkylene$)_xR^5$, $C_1$-$C_3$ alkylene$(SC_1$-$C_4$ alkylene$)_yR^5$, $C_1$-$C_3$ alkylene$(OC_1$-$C_4$ alkylene$)_x(SC_1$-$C_4$ alkylene$)_yR^5$, and $C_1$-$C_3$ alkylene$(SC_1$-$C_4$ alkylene$)_y(OC_1$-$C_4$ alkylene$)_xR^5$;

$R^3$, $R^{3'}$, $R^4$, and $R^{4'}$ are each independently selected from the group consisting of hydrogen, $C_1$-$C_8$ alkyl, $C_2$-$C_8$ alkenyl, and $C_6$-$C_{10}$ aryl;

$R^5$ is selected from the group consisting of hydrogen, $C_1$-$C_8$ alkyl, $C_2$-$C_8$ alkenyl, $C_6$-$C_{10}$ aryl, and a polymeric bulking group;

$R^6$ is $C_1$-$C_{12}$ alkyl or oxo substituted $C_1$-$C_{12}$ alkyl;

a is 0 or 1; and x and y are each independently an integer from 1 to 10.

In some embodiments, $R^6$ is propyl or pentyl. In some embodiments, $R^6$ is pentyl. In some embodiments, $R^6$ is 1-oxopropyl or 1-oxopentyl.

In some embodiments, X is S. In some embodiments, $Z^1$ is O. In some embodiments, $Z^2$ is O. In some embodiments, $Z^1$ and $Z^2$ are each O. In some embodiments, X is S, and $Z^1$ and $Z^2$ are each O.

In some embodiments, $R^1$ and $R^2$ are the same. In some embodiments, $R^1$ and $R^2$ are each independently $C_4$-$C_{10}$ alkyl. In some embodiments, $R^1$ and $R^2$ are each $C_4$-$C_{10}$ alkyl and are the same. In some embodiments, $R^1$ and $R^2$ are each $C_6$-$C_8$ alkyl and are the same. In some embodiments, $R^1$ and $R^2$ are each octyl.

In some embodiments, at least one of $R^1$ and $R^2$ is coupled to the polymeric bulking group. In some embodiments, at least one of $R^1$ and $R^2$ is hydrogen.

In some embodiments, the polymeric bulking group is selected from the group consisting of a silicone, a polyolefin, a polyamide, a polyester, a polycarbonate, a polyaramide, a polyurethane, a polystyrene, an epoxy, a rubber, a starch, a protein, a cellulose, an acrylate, an ABS polymer, a PEEK polymer, a polyol, polyether, polyetherpolyol, and a copolymer of two or more of the foregoing. In some embodiments, the polymeric bulking group is a silicone. In some embodiments, the polymeric bulking group is a silsesquioxane. In some embodiments, the polymeric bulking group is crosslinked.

In some embodiments, $R^1$ is —$(OC_1$-$C_4$ alkyl$)_xR^5$ or $C_1$-$C_3$ alkyl$(OC_1$-$C_4$ alkyl$)_xR^5$. In some embodiments, $R^1$ comprises —$(OC_1$-$C_4$ alkyl$)_x(SC_1$-$C_4$ alkyl$)_yR^5$ or $C_1$-$C_3$ alkyl$(OC_1$-$C_4$ alkyl$)_x(SC_1$-$C_4$ alkyl$)_yR^5$. In some embodiments, $R^1$ is of the formula —$CH_2O(CH_2)_3S(CH_2)_3R^5$.

In some embodiments, the cyclic adduct has a weight of about 200 Da to about 5000 Da. In some embodiments, the cyclic adduct has a weight of about 350 Da to about 5000 Da. In some embodiments, the cyclic adduct has a weight of about 1000 Da to about 5000 Da.

In some embodiments, a is 1.

In some embodiments, $R^3$, $R^{3'}$, $R^4$, and $R^{4'}$ are each hydrogen.

In some embodiments, the cyclic adduct is of the formula

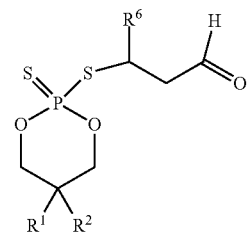

wherein $R^1$ and $R^2$ are each independently hexyl or octyl. In some embodiments, $R^6$ is propyl or pentyl. In some embodiments, $R^6$ is pentyl. In some embodiments, $R^6$ is 1-oxopropyl or 1-oxopentyl.

In some embodiments, the thiol group has a pKa of about 1 to about 4. In some embodiments, the thiol group has a pKa of about 2.5.

In some embodiments, the cyclic adduct is part of a composition that is free of metal thiol chelators. In some embodiments, the composition has a pH of about 2 to about 8. In some embodiments, the composition has a pH of about 2 to about 9. In some embodiments, the composition has a pH of about 7.

In some embodiments, the agent of the sensor coating 306 is a thiol is of the formula III

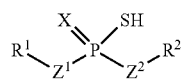

III or a tautomer thereof, wherein

X is S or O;

$Z^1$ and $Z^2$ are each independently O or S;

$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_xR^5$, —$(SC_1$-$C_4$ alkylene$)_yR^5$, —$(OC_1$-$C_4$ alkylene$)_x(SC_1$-$C_4$ alkylene$)_yR^5$, —$(SC_1$-$C_4$ alkylene$)_y(OC_1$-$C_4$ alkylene$)_xR^5$, $C_1$-$C_3$ alkylene$(OC_1$-$C_4$ alkylene$)_xR^5$, $C_1$-$C_3$ alkylene$(SC_1$-$C_4$ alkylene$)_yR^5$, $C_1$-$C_3$ alkylene$(OC_1$-$C_4$ alkylene$)_x(SC_1$-$C_4$ alkylene$)_yR^5$, and $C_1$-$C_3$ alkylene$(SC_1$-$C_4$ alkylene$)_y(OC_1$-$C_4$ alkylene$)_xR^5$;

$R^2$ is selected from the group consisting of $C_3$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_xR^5$, —$(SC_1$-$C_4$ alkylene$)_yR^5$, —$(OC_1$-$C_4$ alkylene$)_x(SC_1$-$C_4$ alkylene$)_yR^5$, —$(SC_1$-$C_4$ alkylene$)_y(OC_1$-$C_4$ alkylene$)_xR^5$, $C_1$-$C_3$ alkylene$(OC_1$-$C_4$ alkylene$)_xR^5$, $C_1$-$C_3$ alkylene$(SC_1$-$C_4$ alkylene$)_yR^5$, $C_1$-$C_3$ alkylene$(OC_1$-$C_4$ alkylene$)_x(SC_1$-$C_4$ alkylene$)_yR^5$, and $C_1$-$C_3$ alkylene$(SC_1$-$C_4$ alkylene$)_y(OC_1$-$C_4$ alkylene$)_xR^5$;

$R^5$ is selected from the group consisting of hydrogen, $C_1$-$C_8$ alkyl, $C_2$-$C_8$ alkenyl, $C_6$-$C_{10}$ aryl, and a polymeric bulking group;

a is 0 or 1; and x and y are each independently an integer from 1 to 10.

In some embodiments, X is S. In some embodiments, $Z^1$ is O. In some embodiments, $Z^2$ is O. In some embodiments, $Z^1$ and $Z^2$ are each O. In some embodiments, X is S, and $Z^1$ and $Z^2$ are each O.

In some embodiments, $R^1$ and $R^2$ are the same. In some embodiments, $R^1$ and $R^2$ are each independently $C_4$-$C_{10}$ alkyl. In some embodiments, $R^1$ and $R^2$ are each $C_4$-$C_{10}$ alkyl and are the same. In some embodiments, $R^1$ and $R^2$ are each independently $C_6$-$C_8$ alkyl In some embodiments, $R^1$ and $R^2$ are each $C_6$-$C_8$ alkyl and are the same. In some embodiments, $R^1$ and $R^2$ are each octyl.

In some embodiments, at least one of $R^1$ and $R^2$ is coupled to the polymeric bulking group. In some embodiments, at least one of $R^1$ and $R^2$ is hydrogen.

In some embodiments, the polymeric bulking group is selected from the group consisting of a silicone, a polyolefin, a polyamide, a polyester, a polycarbonate, a polyaramide, a polyurethane, a polystyrene, an epoxy, a rubber, a starch, a protein, a cellulose, an acrylate, an ABS polymer, a PEEK polymer, a polyol, polyether, polyetherpolyol, and a copolymer of two or more of the foregoing. In some embodiments, the polymeric bulking group is a silicone. In some embodiments, the polymeric bulking group is a silsesquioxane. In some embodiments, the polymeric bulking group is crosslinked.

In some embodiments, $R^1$ is —$(OC_1$-$C_4$ alkyl$)_xR^5$ or $C_1$-$C_3$ alkyl$(OC_1$-$C_4$ alkyl$)_xR^5$. In some embodiments, $R^1$ comprises —$(OC_1$-$C_4$ alkyl$)_x(SC_1$-$C_4$ alkyl$)_yR^5$ or $C_1$-$C_3$ alkyl$(OC_1$-$C_4$ alkyl$)_x(SC_1$-$C_4$ alkyl$)_yR^5$. In some embodiments, $R^1$ is of the formula —$CH_2O(CH_2)_3S(CH_2)_3R^5$.

In some embodiments, the thiol has a weight of about 200 Da to about 5000 Da. In some embodiments, the thiol has a weight of about 350 Da to about 5000 Da. In some embodiments, the thiol has a weight of about 1000 Da to about 5000 Da.

In some embodiments, a is 1.

In some embodiments, the thiol group has a pKa of about 1 to about 4. In some embodiments, the thiol group has a pKa of about 2.5.

In some embodiments, the thiol is part of a composition that is free of metal thiol chelators. In some embodiments, the composition has a pH of about 2 to about 8. In some embodiments, the composition has a pH of about 2 to about 9. In some embodiments, the composition has a pH of about 7.

In some embodiments, when the agent of the sensor coating 306 reacts with the targeted biochemical analyte, an adduct is formed. In some embodiments, the adduct is of the formula II

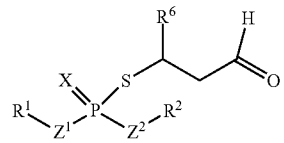

IV or a tautomer thereof, wherein

X is S or O;

$Z^1$ and $Z^2$ are each independently O or S;

$R^1$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_xR^5$, —$(SC_1$-$C_4$ alkylene$)_yR^5$, —$(OC_1$-$C_4$ alkylene$)_x(SC_1$-$C_4$ alkylene$)_yR^5$, —$(SC_1$-$C_4$ alkylene$)_y(OC_1$-$C_4$ alkylene$)_xR^5$, $C_1$-$C_3$ alkylene$(OC_1$-$C_4$ alkylene$)_xR^5$, $C_1$-$C_3$ alkylene$(SC_1$-$C_4$ alkylene$)_yR^5$, $C_1$-$C_3$ alkylene$(OC_1$-$C_4$ alkylene$)_x(SC_1$-$C_4$ alkylene$)_yR^5$, and $C_1$-$C_3$ alkylene$(SC_1$-$C_4$ alkylene$)_y(OC_1$-$C_4$ alkylene$)_xR^5$;

$R^2$ is selected from the group consisting of hydrogen, $C_1$-$C_{12}$ alkyl, $C_2$-$C_{12}$ alkenyl, $C_6$-$C_{10}$ aryl, 5- to 7-membered heteroaryl, —$OR^5$, —$SR^5$, —$(OC_1$-$C_4$ alkylene$)_xR^5$, —$(SC_1$-$C_4$ alkylene$)_yR^5$, —$(OC_1$-$C_4$ alkylene$)_x(SC_1$-$C_4$ alkylene$)_yR^5$, —$(SC_1$-$C_4$ alkylene$)_y(OC_1$-$C_4$ alkylene$)_xR^5$, $C_1$-$C_3$ alkylene$(OC_1$-$C_4$ alkylene$)_xR^5$, $C_1$-$C_3$ alkylene$(SC_1$-$C_4$ alkylene$)_yR^5$, $C_1$-$C_3$ alkylene$(OC_1$-$C_4$ alkylene$)_x(SC_1$-$C_4$ alkylene$)_yR^5$, and $C_1$-$C_3$ alkylene$(SC_1$-$C_4$ alkylene$)_y(OC_1$-$C_4$ alkylene$)_xR^5$;

$R^5$ is selected from the group consisting of hydrogen, $C_1$-$C_8$ alkyl, $C_2$-$C_8$ alkenyl, $C_6$-$C_{10}$ aryl, and a polymeric bulking group;

$R^6$ is $C_1$-$C_{12}$ alkyl or oxo substituted $C_1$-$C_{12}$ alkyl;

a is 0 or 1; and x and y are each independently an integer from 1 to 10.

In some embodiments, $R^6$ is propyl or pentyl. In some embodiments, $R^6$ is pentyl. In some embodiments, $R^6$ is 1-oxopropyl or 1-oxopentyl.

In some embodiments, X is S. In some embodiments, $Z^1$ is O. In some embodiments, $Z^2$ is O. In some embodiments, $Z^1$ and $Z^2$ are each O. In some embodiments, X is S, and $Z^1$ and $Z^2$ are each O.

In some embodiments, $R^1$ and $R^2$ are the same. In some embodiments, $R^1$ and $R^2$ are each independently $C_4$-$C_{10}$ alkyl. In some embodiments, $R^1$ and $R^2$ are each $C_4$-$C_{10}$ alkyl and are the same. In some embodiments, $R^1$ and $R^2$ are each independently $C_6$-$C_8$ alkyl. In some embodiments, $R^1$ and $R^2$ are each $C_6$-$C_8$ alkyl and are the same. In some embodiments, $R^1$ and $R^2$ are each octyl.

In some embodiments, at least one of $R^1$ and $R^2$ is coupled to the polymeric bulking group. In some embodiments, at least one of $R^1$ and $R^2$ is hydrogen.

In some embodiments, the polymeric bulking group is selected from the group consisting of a silicone, a polyolefin, a polyamide, a polyester, a polycarbonate, a polyaramide, a polyurethane, a polystyrene, an epoxy, a rubber, a starch, a protein, a cellulose, an acrylate, an ABS polymer, a PEEK polymer, a polyol, polyether, polyetherpolyol, and a copolymer of two or more of the foregoing. In some embodiments, the polymeric bulking group is a silicone. In some embodiments, the polymeric bulking group is a silsesquioxane. In some embodiments, the polymeric bulking group is crosslinked.

In some embodiments, $R^1$ is —$(OC_1$-$C_4$ alkyl$)_xR^5$ or $C_1$-$C_3$ alkyl$(OC_1$-$C_4$ alkyl$)_xR^5$. In some embodiments, $R^1$ comprises —$(OC_1$-$C_4$ alkyl$)_x(SC_1$-$C_4$ alkyl$)_yR^5$ or $C_1$-$C_3$ alkyl$(OC_1$-$C_4$ alkyl$)_x(SC_1$-$C_4$ alkyl$)_yR^5$. In some embodiments, $R^1$ is of the formula —$CH_2O(CH_2)_3S(CH_2)_3R^5$.

In some embodiments, the adduct has a weight of about 200 Da to about 5000 Da. In some embodiments, the adduct has a weight of about 350 Da to about 5000 Da. In some embodiments, the adduct has a weight of about 1000 Da to about 5000 Da.

In some embodiments, a is 1.

As described above, the agent of the sensor coating 306 is configured to react with the targeted biochemical analyte to produce a product that has a higher molecular weight. In use, the initial increase in sensor mass detected on the surface of the quartz crystal resonator 230 is determined based on the sensor data. As discussed above, in the illustrative embodiment, the sensor data includes the frequency of the oscillating quartz crystal resonator 230, and the change in frequency is generally proportional to the change in sensor mass. Accordingly, the initial increase in sensor mass is determined by measuring the change in frequency of the oscillating quartz crystal resonator 230 as discussed in detail below.

In some embodiments, the initial increase in sensor mass may also be determined based on an absolute mass change. To do so, a current surface mass and an initial surface mass on the quartz crystal resonator 230 prior to the reaction may be compared to measure the initial increase in sensor mass. It should be appreciated that the detection of a subsequent increase in sensor mass is determined by comparing the current surface mass and a subsequent surface mass on the quartz crystal resonator 230.

The mass change generally correlates to the concentration of targeted biochemical analyte detected on the quartz crystal resonator 230. However, it should be appreciated that the amount of the agent available to react with the targeted biochemical analyte may influence the reaction rate, thereby affecting the mass change and/or the mass change rate detected on the surface of the quartz crystal resonator 230. Such mass increase associated with the reaction is detected by the controller 212 of the pest control device 102, which is discussed in detail in FIGS. 6 and 8.

In some embodiments, the mass change rate may be influenced by a detection response time of the sensor 210. The detection response time may increase if an accumulation of the targeted biochemical analyte in air surrounding the sensor 210 is required in order to generate a signal or sensor data that amounts to a measurable change indicative of a presence of bed bugs. In other words, at low concentration of the targeted biochemical analyte, the mass change of the quartz crystal resonator 230 resulted from the reaction may not be sufficient until the targeted biochemical analyte is accumulated to a predetermined amount. In some embodiments, a pre-concentrator may be used to reach a minimum predetermined amount of the targeted biochemical analyte such that the sensor 210 can immediately detect a low concentration of the targeted biochemical analyte.

It should be noted that the amount of the agent of the sensor coating 306 decreases as the agent reacts with the targeted biochemical analyte. It should be appreciated that, in some embodiments, the reaction is reversible from the product to the agent based on heat. In such embodiments, the pest control device 120 further includes a heating element (not shown). When the amount of the agent of the sensor coating 306 reaches a threshold level, the pest control device 120 applies heat to the quartz crystal resonator 230 to reverse the reaction and recover the agent of the sensor coating 306. In some embodiments, the pest control device 120 may generate a local or remote alert indicating that the sensor 210 requires maintenance to replenish the agent of the sensor coating 306 or replace the quartz crystal resonator 230 or the sensor 210.

Referring back to FIG. 2, the controller 212 may be embodied as any type of controller, circuit, or component capable of performing the functions described herein. The controller 212 is configured to determine the presence of bed bugs by analyzing sensor data produced by the sensor 210. Specifically, in the illustrative embodiment, the quartz crystal resonator 230 of the sensor 210 generates sensor data. The sensor data includes, among other things, mass changes on the surface of the quartz crystal resonator 230. It should be appreciate that the mass change on the quartz crystal resonator 230 indicates that the agent of the sensor coating 306 of the quartz crystal resonator 230 is being converted to a product that has a different molecular weight, and the mass change rate is generally proportional to the rate of reactions to convert the agent into the product.

As discussed above, in the illustrative embodiment, the product resulting from the reaction between the agent (e.g., dioctyl-CTI) and the targeted biochemical analyte, such as T2H, T2O, 4-oxo-(E)-2-hexenal, and/or 4-oxo-(E)-2-octenal, has a higher molecular weight compared to the molecular weight of the dioctyl-CTI. Accordingly, the controller 212 determines whether the mass increase exceeds a predefined threshold rate. The predefined threshold rate is a base mass change rate in the presence of bed bugs. For example, in some embodiments, the base mass change may be a minimum mass change rate in the presence of bed bugs. In other embodiments, the base mass change may be a minimum mass change rate plus some additional safety factor to avoid false positives or unwanted detections. For example, in some cases, environmental factors, such as temperature and humidity in air surrounding the sensor 210, may affect the accuracy of the mass change rate detected and result in sensor drift. The inclusion of some additional safety factors may compensate for unpredicted environmental effects to decrease unwanted detections due to sensor drift.

As discussed above, the initial increase in sensor mass detected on the surface of the quartz crystal resonator 230 is determined by measuring the change in frequency of the oscillating quartz crystal resonator 230. In some embodiments, as discussed above, the initial increase in sensor mass may also be determined based on an absolute mass change by comparing a current mass on the quartz crystal resonator 230 and an initial mass on the quartz crystal resonator 230 prior to the reaction. It should be appreciated that the detection of a subsequent mass increase is determined by comparing the current mass of the quartz crystal resonator 230 and a subsequent mass of the quartz crystal resonator 230. It should be appreciated that, in some embodiments, the sensor data may be processed at the server 104.

In some embodiments, the sensor 210 may detect the presence of bed bugs by detecting the decrease in sensor mass upon heating the quartz crystal resonator 230. To do so, the sensor 210 may determine the mass detected on the surface of the quartz crystal resonator 230 before and after applying the heat to the quartz crystal resonator 230 and determine whether a change in mass exceeds a predefined threshold. As discussed above, when the heat is applied to the quartz crystal resonator 230, the product resulted from the reaction between the agent and the targeted biochemical analyte releases the targeted biochemical analyte and results in decrease in sensor mass to detect the presence of bed bugs In some embodiments, the sensor 210 may determine both the mass gain and mass loss to eliminate false positives or unwanted detections. For example, in some cases, environmental factors, such as dust or other particles in air surrounding the sensor 210 may interact with the agent of the sensor coating 306 and increase the sensor mass detected on the surface of the quartz crystal resonator 230. In such embodiments, the sensor 210 may identify false positives or unwanted detections if the increase in the sensor mass prior to the heating exceeds a first predefined threshold while the decrease in the sensor mass after the heating does not exceed a second predefined threshold.

The power source 214 may be embodied as any type of device, circuit, or component capable of providing electrical power to the components of the pest control device 120, such as the controller 212, the sensor 210, the wireless communication circuit 216, the local indicator 218, or the fan 220 as needed. In some embodiments, the power source 214 may be electrochemical cells or a battery.

The wireless communication circuit 216 may be embodied as any type of device, circuit, or component capable of enabling communications between the pest control device 104 and the gateway 122. Each pest control device 120 is configured to periodically or continually communicate with the gateway 122 to transmit the sensor data to the server 104 using the network 106. For example, the sensor data may include, among other things, notifications such as a detection of bed bug and/or an indication that the sensor requires a maintenance. To do so, the wireless communication circuit 216 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The local indicator 218 may be embodied as any type of indicator that is capable of generating an alert to notify a human operator or a technician. For example, the local indicator 218 may be embodied as a visual and/or audible indicator. In some embodiments, the visual indicator 218 may include a light emitting diode (LED), fluorescent, incandescent, and/or neon type light source. The audible indicator may generate an alert sound to notify the technician. In the illustrative embodiment, the local indicator 218 generates an alert indicative of a presence or absence of bed bugs. For example, in some embodiments, the LED light indicator 218 may be energized to project a colored light, change color, or change from a non-blinking light to a blinking light to indicate the presence of bed bugs. In other embodiments, the audible local indicator 218 may generate sound to indicate the presence of bed bugs.

In some embodiments, the local indicator 218 may also output a signal indicative of whether the sensor 230 requires maintenance. For example, the local alert may indicate a malfunction of the sensor 230. In some embodiments, the local alert may indicate the depletion of the agent of the sensor 210. In such embodiments, the LED light indicator 218 may be energized to project a colored light, change color, or change from a non-blinking light to a blinking light to indicate the presence of bed bugs. It should be appreciated that the color of the LED light indicator 218 indicating the sensor maintenance may be different from the color of the LED light indicator 218 indicating the bed bug detection. In some embodiments, the visual indicator may be used to indicate the presence of bed bugs and an audible indicator may be used to indicate that the sensor 210 requires maintenance or vice versa.

It should be appreciated that, in some embodiments, the pest control device 120 may further include a handle (not shown) on a housing member 202 to provide a grip to a human operator or a technician. The technician may grip the handle of the pest control device 120 and manually move the pest control device 120 to identify a localized area of the targeted biochemical analyte indicative of a presence of bed bugs.

Figure 4:
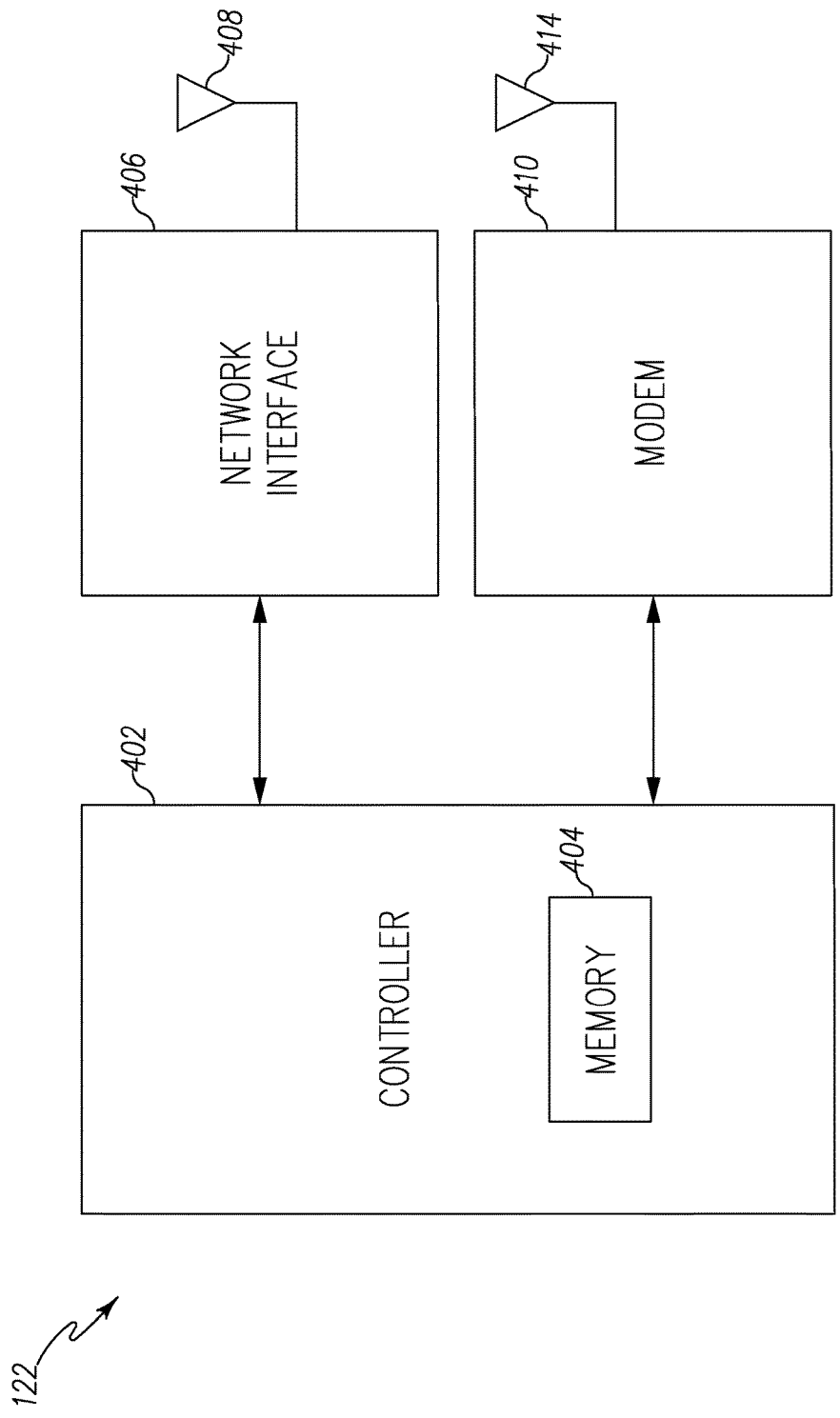
FIG. 4 is a diagrammatic view of at least one embodiment of a gateway of the pest control system of FIG. 1.

Referring now to FIG. 4, the gateway 122 includes a controller 402 with a memory 404, a wireless network interface 406 with an antenna 408, and a modem 412 with an antenna 414. The controller 402 may be embodied as any type of controller, circuit, or component capable of performing the functions described herein including, without limitation, a computer, a multiprocessor system, a laptop computer, a notebook computer, a tablet computer, a wearable computing device, a network appliance, a web appliance, a distributed computing system, a processor-based system, and/or a consumer electronic device. In some embodiments, the controller 402 may be of a microcontroller type, such as model no. C805F120 provided by Cygnal Technologies.

The memory 404 may be embodied as any type of volatile or non-volatile memory or data storage capable of performing the functions described herein. In operation, the memory 404 may store various data and software used during operation of the gateway 122 such as programs, libraries, and drivers. In some embodiments, the memory 404 may temporarily store and aggregate sensor data received from the pest control devices 120 prior to transmitting the sensor data to the server 104 over the network 106.

In the illustrative embodiment, the modem 412 with the antenna 414 is configured to interface with a cellular network or a wireless WAN network 106 to communicate with network 106. In some embodiments, the modem 408 may utilize General Packet Radio Service (GPRS) through a Global System for Mobile communications (GSM) protocol. In some embodiments, the model 408 may be of a hardwired dial-up and/or coaxial cable type.

In the illustrative embodiment, the wireless network interface 406 with the antenna 408 is configured to interface with a wireless communication network as defined by a corresponding pest control group 102 to communicate with the pest control devices 120. In some embodiments, the wireless communication network may be a local area network (LAN) type.

Figure 5:
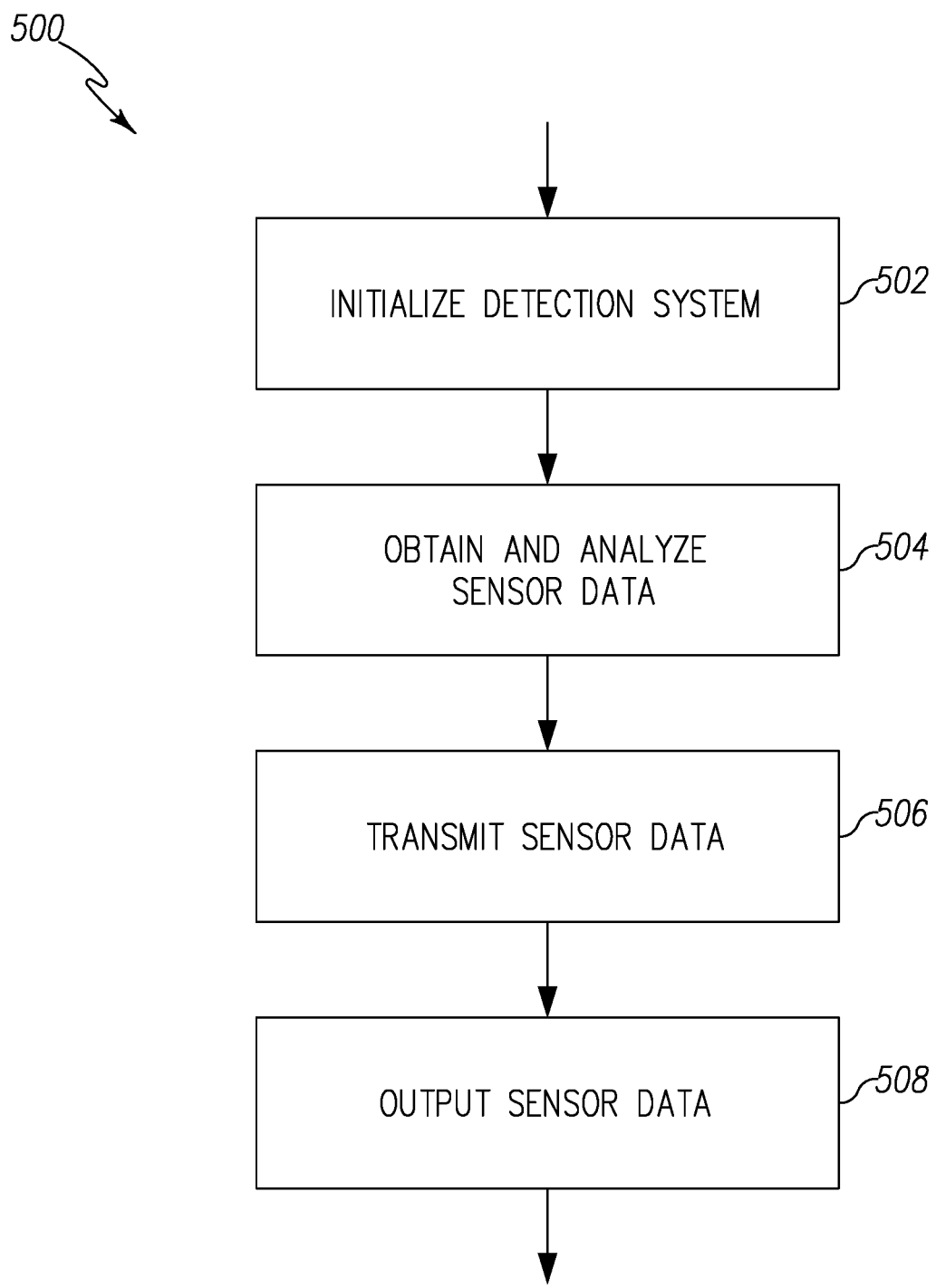
FIG. 5 is a simplified flow chart of a control routine of the pest control system of FIG. 1.

Referring now to FIG. 5, in use, the pest control system 100 may execute a routine 500 for detecting a presence of bed bugs. The routine 500 begins with block 502 in which the communication components of pest control system 100 are initialized to form new communication paths from each of the pest control device 120 to the server 104 or the client compute device 108. For example, the wireless network interface 406 and the modem 412 of the gateway 122 may be initialized to establish links to networks.

In block 504, each of the pest control device 120 obtains and analyzes data generated by the sensor 210 of the pest control device 120. As described above, in the illustrative embodiment, the sensor 210 includes a quartz crystal resonator 230 that is configured to output sensor data, and a surface of the quartz crystal resonator 230 has the sensor coating 306, which includes the agent. As discussed above, the agent of the sensor coating 306 selectively reacts with the targeted biochemical analyte secreted by pests. During the reaction, the agent is converted to a product with a different molecular weight compared to the molecular weight of the agent. As discussed above, the quartz crystal resonator 230 outputs sensor data that includes a frequency of oscillation, which is indicative of the mass changes on the surface of the quartz crystal resonator 230. As discussed above, the change in frequency is generally proportional to the change in sensor mass deposited on the surface of the quartz crystal resonator 230. Accordingly, the controller 212 of the pest control device 120 analyzes the sensor data of the quartz crystal resonator 230 and determines a presence of pests based on a level of mass change, which is discussed in detail in FIGS. 6 and 7.

In some embodiments, the sensor data may include a status of the sensor 210. For example, the status of the sensor 210 may include an amount of remaining agent of the sensor coating 306. As discussed above, the frequency of oscillation of the quartz crystal resonator 230 partially depends on the mass of the agent coated on the quartz crystal resonator 230. As such, the remaining agent coated on the quartz crystal resonator 230 may be estimated based on the frequency of oscillation of the quartz crystal resonator 230. In other embodiments, each of the pest control device 120 may determine an amount of the agent that has been converted to the product, thereby determine the amount of the agent remaining in the sensor coating 306. It should be appreciated that having a sufficient amount of the agent of the sensor coating 306 is necessary for accurate detection of the presence of pests.

In block 506, the sensor data of the pest control device 120 is transmitted to the pest data management server 104. To do so, the pest control device 120 transmits the sensor data to the gateway 122. The gateway 122 subsequently transmits the sensor data to the server 104 via the network 106.

In block 508, the server 104 outputs the sensor data. In some embodiments, the server 104 may perform corresponding actions using the application 140. For example, the application 140 includes a notifications and alarm service that can dispatch alerts to the client compute device 108 based on conditions set within the database 142.

Figure 6:
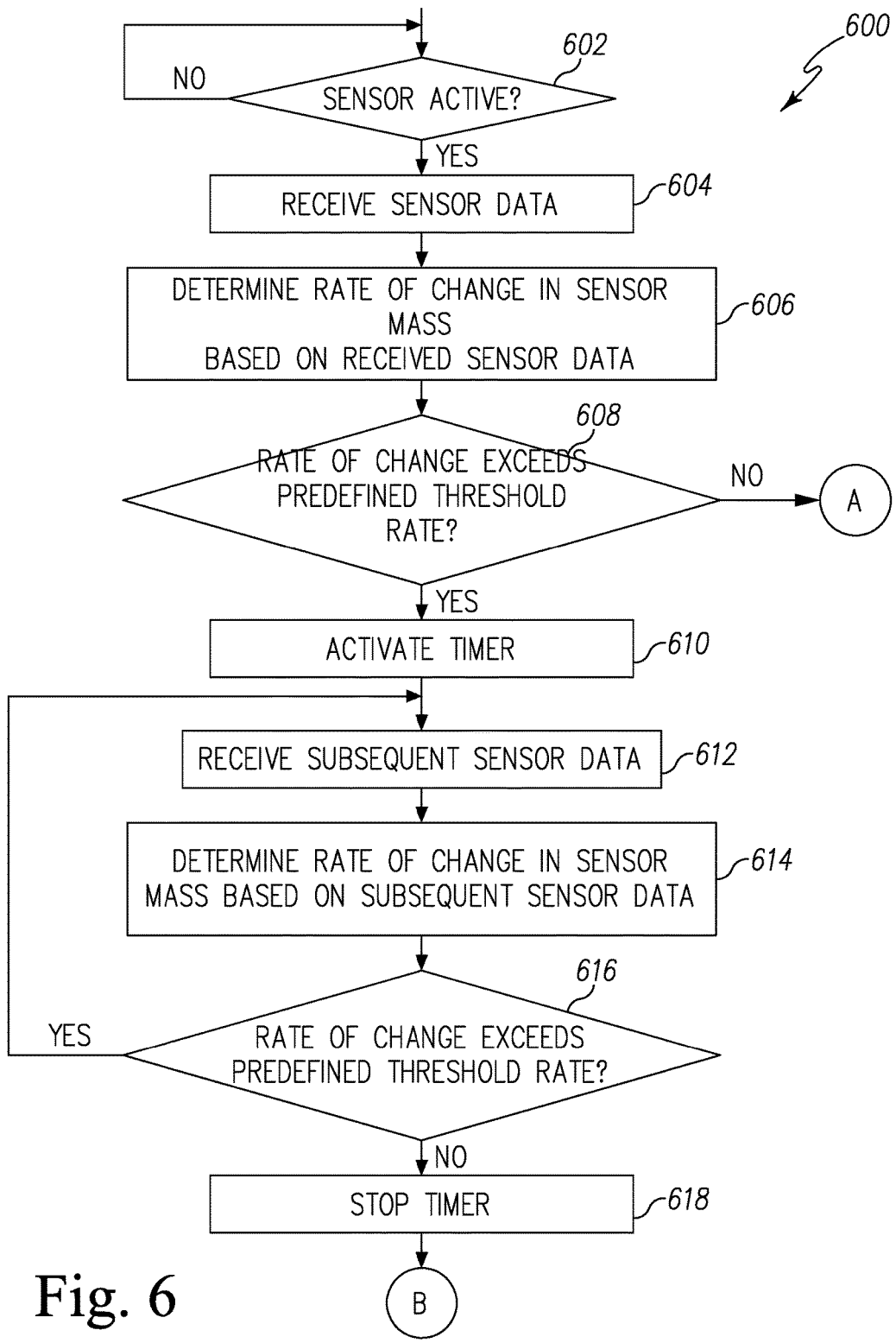
FIGS. 6 and 7 are simplified flow charts of a first embodiment of a control routine of the pest control system of FIG. 1.
Figure 7:
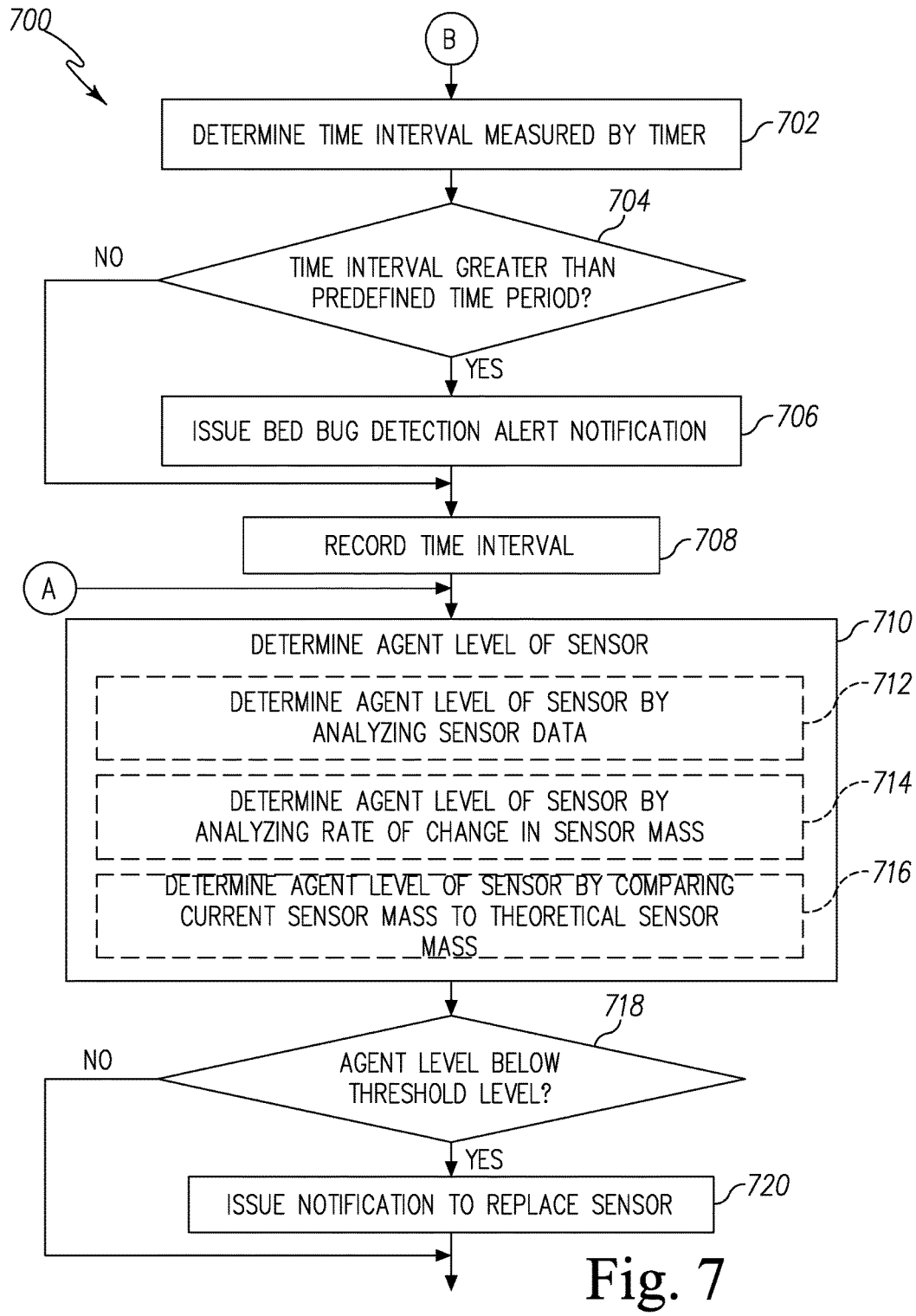

Referring now to FIGS. 6 and 7, in use, the controller 212 of the pest control device 120 may execute a routine 600 for detecting a presence of bed bugs by determining rate of changes in sensor mass and a routine 700 for determining whether to issue an alert notification. The routine 600 begins with block 602 in which the controller 212 determines whether the sensor 210 of the pest control device 120 is active. If the controller 212 determines that the sensor 210 is not active, the routine 600 loops back to block 602 to continue monitoring for an active sensor 210. If, however, the controller 212 determines that the sensor 210 is active, the routine 600 advances to block 604.

In block 604, the controller 212 receives sensor data from the sensor 210. In the illustrative embodiment, the sensor or quartz crystal microbalance 210 generates sensor data indicative of mass changes on the surface of the quartz crystal resonator 230 of the quartz crystal microbalance 210. As described above, the sensor data includes the frequency of oscillation of quartz crystal resonator 230, which is generally proportional to the change in sensor mass. Based on the received sensor data, in block 606, the controller 212 determines a rate of change in sensor mass (i.e., the mass change rate on the surface of the quartz crystal resonator 230).

In block 608, the controller 212 determines whether the determined rate of change in the sensor mass exceeds a predefined threshold rate. It should be appreciated that the predefined threshold rate is the base mass change rate in the presence of bed bugs and is used to reduce false positive detection of bed bugs. As discussed above, the base mass change rate is a minimum mass change rate in the presence of bed bugs. In some embodiments, the base mass change may be a minimum mass change rate plus some additional safety factor to avoid false positives or unwanted detections.

If the controller 212 determines that the rate of change does not exceeds the predefined threshold rate, the controller 212 determines that no bed bug is detected, and the routine 600 skips ahead skips to block 710 of the routine 700 shown in FIG. 7, which is described in detail below. If, however, the controller 212 determines that the rate of change exceeds the predefined threshold rate, the routine 600 advances to block 610. In block 610, the controller 212 activates or starts a timer when the rate of change in sensor mass exceeds the predefined threshold rate. It should be appreciated that, in some embodiments, the controller 212 may record a start time at which the rate of change in sensor mass exceeded the predefined threshold rate. In other words, the start time is the time at which the pest control device 108 detected a presence of bed bugs.

To further reduce false positive detection of bed bugs, the controller 212 determines how long the mass change rate has exceeded the predefined threshold rate. To do so, the controller 212 receives subsequent sensor data from the sensor 210 in block 612. Based on the subsequent sensor data, the controller 212 determines a rate of change in sensor mass in block 614.

In block 616, the controller 212 determines whether the rate of change based on the subsequent sensor data still exceeds the predefined threshold rate. If the controller 212 determines that the rate of change exceeds the predefined threshold rate, the routine 600 loops back to block 612 to continue to receive subsequent sensor data. If, however, the controller 212 determines that the rate of change does not exceed the predefined threshold rate, the routine 600 advances to block 618.

In block 618, the controller 212 stops the timer. It should be appreciated that, in some embodiments, the controller 212 records an end time at which the rate of change exceeded the predefined threshold rate. In other words, the end time is the time at which the pest control device 108 no longer detects a presence of bed bugs. The routine 600 subsequently proceeds to block 702 of the routine 700 shown in FIG. 7 to determine whether to issue an alert notification.

In block 702 shown in FIG. 7, the controller 212 determines a time interval measured by the timer. It should be appreciated that the determined time interval indicates the time period that the bed bugs have been detected.

In block 704, the controller 212 determines whether the time interval is greater than a predefined time period. As discussed above, the predefined time period is used to reduce false positive detection. If the time interval is less than the predefined time period, the controller 212 determines that such detection is likely be a false positive, and the routine 700 skips ahead to block 708 in which the controller 212 records the time interval. The false positive may be due to, for example, unexpected environmental factors, unexpected malfunctioning of the device, and/or human error.

If, however, the controller 212 determines that the time interval is greater than the predefined time period, the routine 700 advances to block 706. In block 706, the controller 212 issues a bed bug detection alert notification. In some embodiments, the controller 212 may issue the local bed bug detection alert notification via the local indicator 218. In other embodiments, the controller 212 may issue the bed bug detection alert notification to the server 104. In block 708, the controller 212 records the time interval.

Subsequent to detecting the presence of bed bugs, the controller 212 further determine an agent level of the sensor coating 306 on the quartz crystal resonator 230 of the sensor 210 to determine when to replenish the sensor coating 306 on the quartz crystal resonator 230 or replace the quartz crystal resonator 230 and/or the sensor 210. It should be appreciated that, in some embodiments, the controller 212 may simultaneously determine the agent level and a presence of bed bug.

In block 710, the controller 212 determines a level of the agent of the sensor coating 306 on the quartz crystal resonator 230. To do so, in some embodiments, in block 712, the controller 212 may determine the agent level based on the sensor data. As discussed above, the frequency of oscillation of the quartz crystal resonator 230 is partially dependent on the mass of the agent coated on the quartz crystal resonator 230. As such, the controller 212 may estimate the amount of remaining agent based on the frequency of oscillation of the corresponding quartz crystal resonator 230.

In some embodiments, in block 714, the controller 212 may determine the agent level by analyzing the rate of changes in sensor mass. For example, the controller 212 determines the rate of changes in the sensor mass over a predetermined period of time and calculate a total mass change over the predetermined period of time. It should be appreciated that the total mass change is a weight difference between a weight of the product produced over the predetermined period of time and a weight of agent that reacted with the targeted biochemical analyte to produce the product. The controller 212 may calculate the amount of the agent that has been consumed in the reaction from the total mass change. Accordingly, the controller 212 may determine the amount of agent remaining on the quartz crystal resonator 230 available to react with the targeted biochemical analyte.

In some embodiments, in block 716, the controller 212 may determine the agent level of the sensor 210 by comparing the current sensor mass to a theoretical sensor mass. The theoretical sensor mass is a sensor mass that is expected if all amount of the agent of the sensor coating 306 is converted to the product.

In block 718, the controller 212 determines whether the agent level is below a threshold level. The threshold level is set based on a minimum amount of agent in the sensor coating 306 required to react with the targeted biochemical analyte. In other words, if the agent level is below the threshold level, the agent is depleted, and no further reaction can occur.

If so, the routine 700 advances to block 720 in which the controller 212 issues a notification to replace the sensor 210. In some embodiments, the controller 212 may issue the local replacement notification via the local indicator 218. In other embodiments, the controller 212 may issue the notification to the server 104.

If, however, the controller 212 determines that the agent level is higher than the threshold level, the routine 700 skips block 720. The routine 700 may loop back to block 604 of the routine 600 in FIG. 6 to continue receiving sensor data to determine the presence of bed bugs and the agent level of the sensor 210.

Figure 8A:
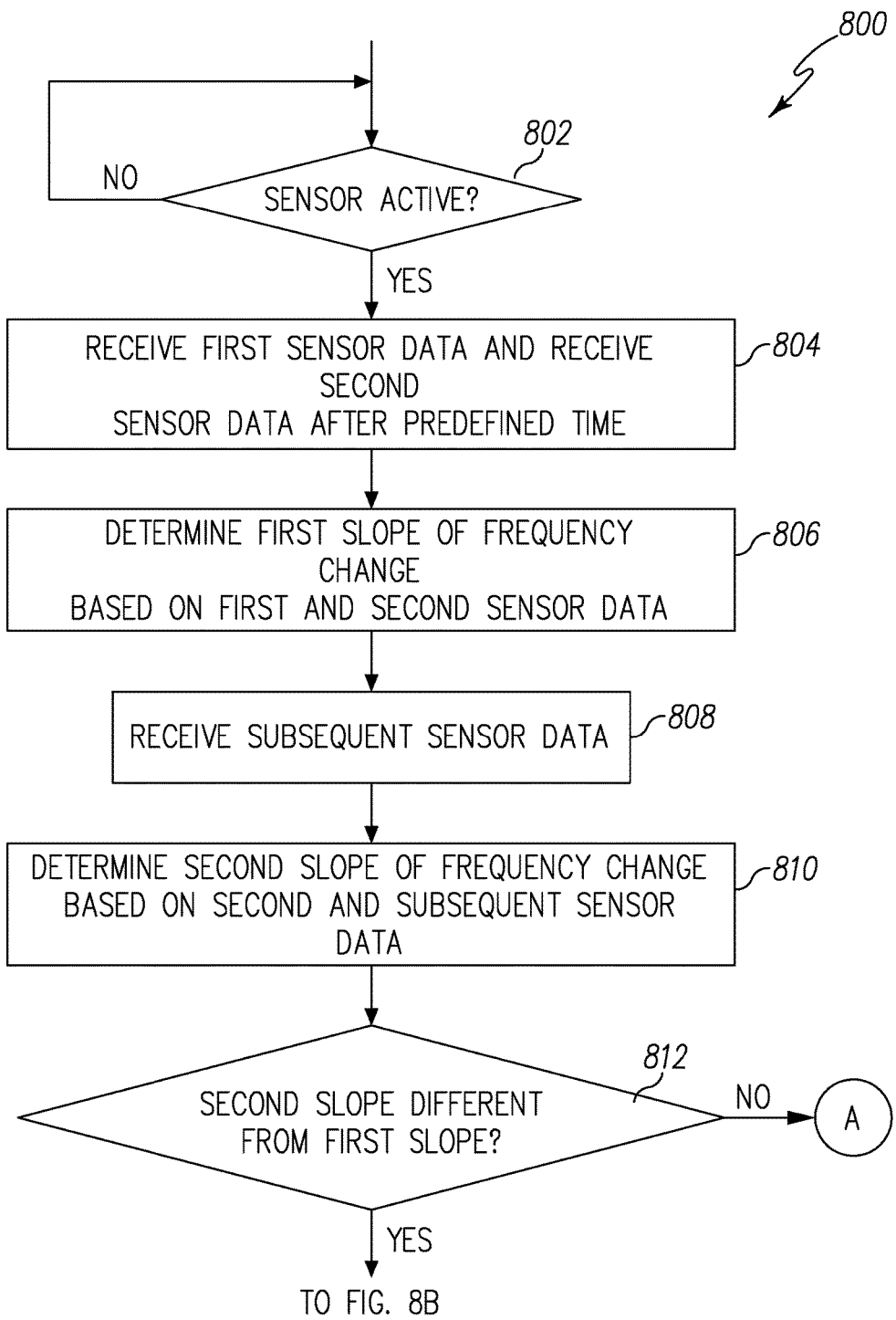
FIGS. 8A and 8B are simplified flow charts of a second embodiment of a control routine of the pest control system of FIG. 1.
Figure 8B:
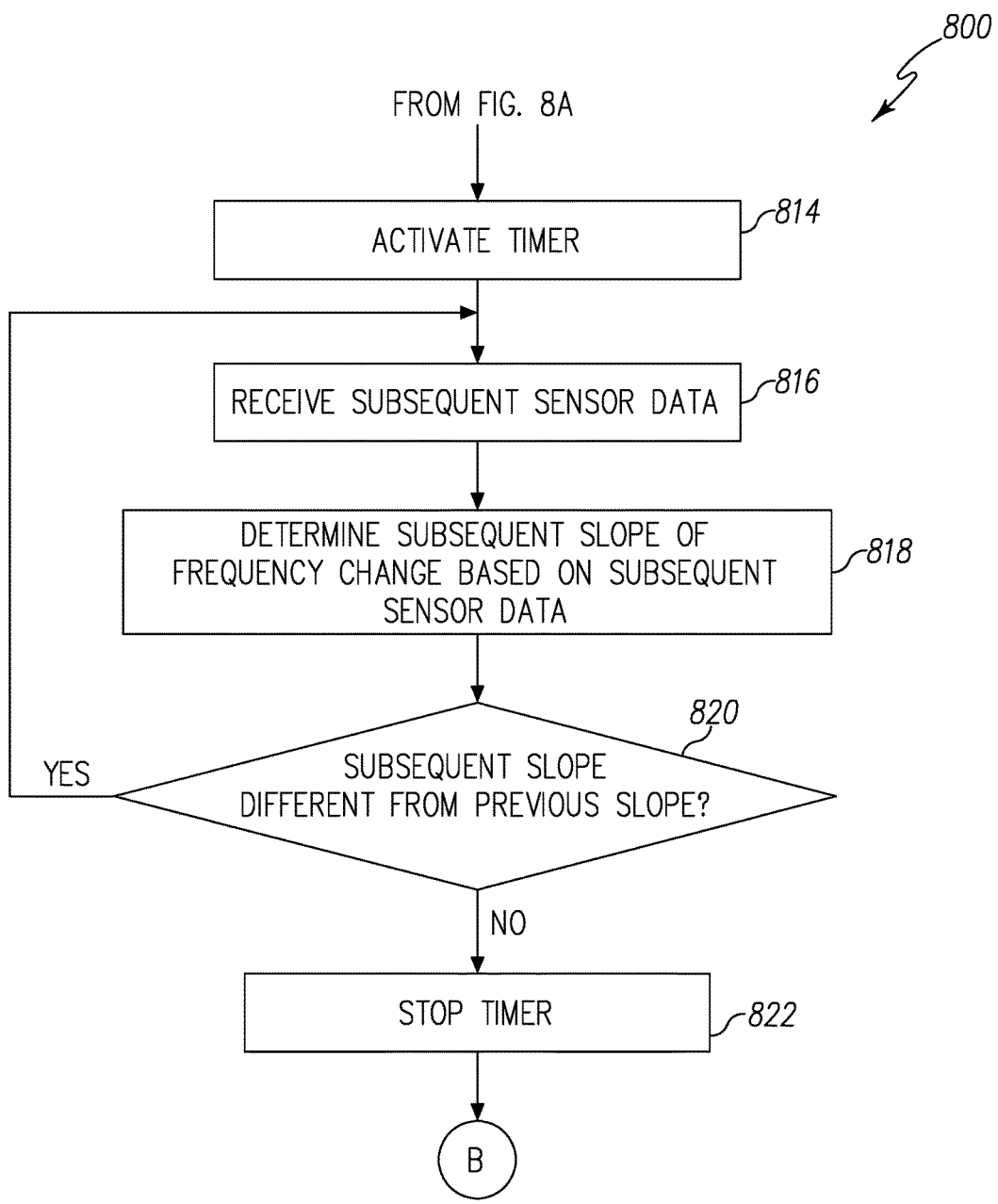

Referring now to FIGS. 8A and 8B, in use, the controller 212 of the pest control device 120 may execute an alternative routine 800 alternative to the routine 600 for detecting a presence of bed bugs by comparing the rate of change in frequency over time. The routine 800 begins with block 802 in which the controller 212 determines whether the sensor 210 of the pest control device 120 is active. If the controller 212 determines that the sensor 210 is not active, the routine 800 loops back to block 802 to continue monitoring for an active sensor 210. If, however, the controller 212 determines that the sensor 210 is active, the routine 800 advances to block 804.

In block 804, the controller 212 receives first sensor data and subsequently receives second sensor data after a predefined time. As discussed above, in the illustrative embodiment, the sensor data includes the frequency of the oscillating quartz crystal resonator 230. Accordingly, in block 806, the controller 212 determines a first slope of frequency change (i.e., a rate of change in frequency) during the predefined time based on the first and second sensor data. However, it should be appreciated that in other embodiments, the controller 212 determines a first slope of any signal change based on the first and second sensor data.

Subsequently, in block 808, the controller 212 further receives subsequent sensor data after the predefined time. The controller 212 then determines a second slope of frequency change based on the second and subsequent sensor data in block 810.

In block 812, the controller 212 determines whether the second slope is different from the first slope. In other words, the controller 212 compares the first and second rate of changes in frequency. As discussed above, the change in frequency is indicative of the change in sensor mass. It should be noted, however, that the sensitivity and/or accuracy of the sensor detection may decrease due to sensor drift over time and may prevent the controller 212 from detecting the presence of low-level targeted biochemical analyte. As such, by calculating the difference in the rates of frequency change to determine the presence of bed bugs, the controller 212 may minimize the influence of possible sensor drift when monitoring for long periods of time.

If the controller 212 determines that the second slope is not different from the first slope (i.e., the rate of change in frequency has not changed), the controller 212 determines that no bed bug is detected, and the routine 800 skips to block 710 of the routine 700 shown in FIG. 7.

If, however, the controller 212 determines that the second slope is different from the first slope, the routine 800 advances to block 814 shown in FIG. 8B which the controller 212 activates a timer to indicate a start time at which the controller 212 detected an abrupt change in frequency. In other words, the start time is the time at which the pest control device 108 detected a presence of bed bugs.

To further reduce false positive detection of bed bugs, the controller 212 determines how long the rate of change in frequency (i.e., the rate of change in sensor mass) is changing. To do so, the controller 212 receives subsequent sensor data from the sensor 210 in block 612. Based on the subsequent sensor data, the controller 212 determines a subsequent slope of frequency change in block 818.

In block 820, the controller 212 determines whether the subsequent slope is different from a previous slope. It should be appreciated that the previous slope is a slope that was determined immediately prior to the subsequent slope. If the controller 212 determines that the slope has changed, the routine 800 loops back to block 816 to continue to receive subsequent sensor data. If, however, the controller 212 determines that the slope has not changed, the routine 800 advances to block 822.

In block 822, the controller 212 stops the timer to indicate an end time at which the controller 212 detected no change in frequency. In other words, the end time is the time at which the pest control device 108 no longer detects a presence of bed bugs. The routine 800 then advances to block 702 of the routine 700 shown in FIG. 7 to determine whether to issue a bed bug detection alert notification based on the time interval between the start time and end time, which is discussed in detail above.

It should be appreciated that the sensor 210 may be embodied as other types of sensors that are capable of detecting the targeted biochemical analyte. For example, as discussed above, the sensor 210 may be embodied as a cantilever sensor. In such embodiments, the cantilever sensor includes a body and one or more cantilevers that project outwardly from the body. Each cantilever is coated with the agent, which reacts with the targeted biochemical analyte, and is configured to oscillate in a vertical direction. To initiate the oscillation of each cantilever, the cantilever sensor may be excited by resistive heating to cause a layer thermal expansion mismatch. When the agent of the oscillating cantilever reacts with the targeted biochemical analyte, the resonant frequency of the oscillating cantilever changes due to increase in mass on the cantilever. As discussed above, the frequency change may be used to detect the presence of bed bugs. In some embodiments, the cantilever sensor may further include a piezoresistive pressure sensor. In such embodiments, the piezoresistive pressure sensor measures a degree of deformation (e.g., bending) of the cantilever during the oscillation and determines the presence of bed bugs if the degree of deformation is greater than a predefined threshold.

Referring now to FIGS. 9-12, another embodiment of a pest control device (hereinafter pest control device 890) is shown. In the illustrative embodiment, the pest control device 890 includes a sensor 908 that is positioned in a harborage device 900. It should be appreciated that the sensor 908 may take the form of the sensor 210 described above in reference to FIGS. 1-8 or any of the other sensors described above. The harborage device 900 is configured to create favorable conditions to attract pests (e.g., color, temperature, texture, and/or odor that appeals to targeted pests) to cause them to enter and congregate in the harborage device. For example, in the illustrative embodiment, the harborage device 900 includes a light blocking material to attract pests such as, for example, bed bugs, that prefer a dark and shady environment. Additionally, in the illustrative embodiment, the harborage device 900 includes an attractive color that appeals to the targeted pests.

Figure 9:
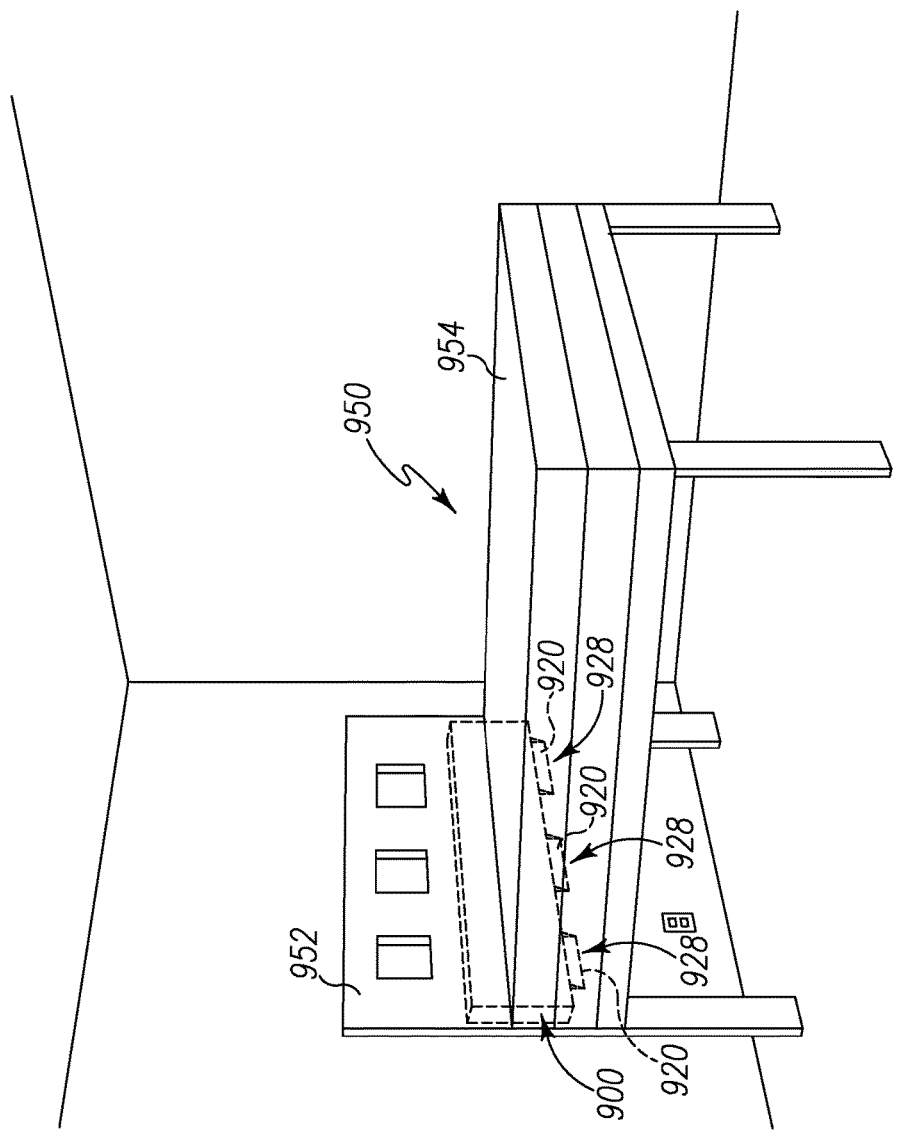
FIG. 9 is an elevation view of an another embodiment of a pest control device attached to a headboard of a bed.

As shown in FIG. 9, the harborage device 900 is configured to be secured to a bed headboard 952 of a bed 950. For example, the harborage device 900 may be secured to a surface of the bed headboard 952 that faces away from the bed mattress 954 and toward the wall of the room. Such a harborage device 900 is configured to attract pests that have a preferred habitat near beds or mattresses, for example, bed bugs. It should be appreciated that, in some embodiments, the harborage device 900 may be secured to any surface of the bed 950 using a fastener or adhesive that do not produce volatile compounds that may react with the targeted analyte or otherwise interfere with the sensor. In other embodiments, the harborage device 900 may be placed near the bed 950 or any other environment that is prone to pest infestation.

The harborage device 900 includes an inner chamber 940 and a plurality of inlets 928 that open into the chamber 940 to permit entry of the pests. It should be appreciated that each inlet 928 is sized to allow easy access for pests and provide oxygen within the harborage device 900 for harboring the pests. To do so, the width of each inlet 928 may be determined based on the size of the targeted pests to ensure that each inlet 928 is sized to allow entrance of the targeted pests while reducing unnecessary diffusional losses of the targeted analyte to the environment of the harborage device 900. For example, if the harborage device 900 is configured to detect the presence of bed bugs, the optimal width of each inlet 928 may range from 3 mm to 100 mm.

Figure 10:
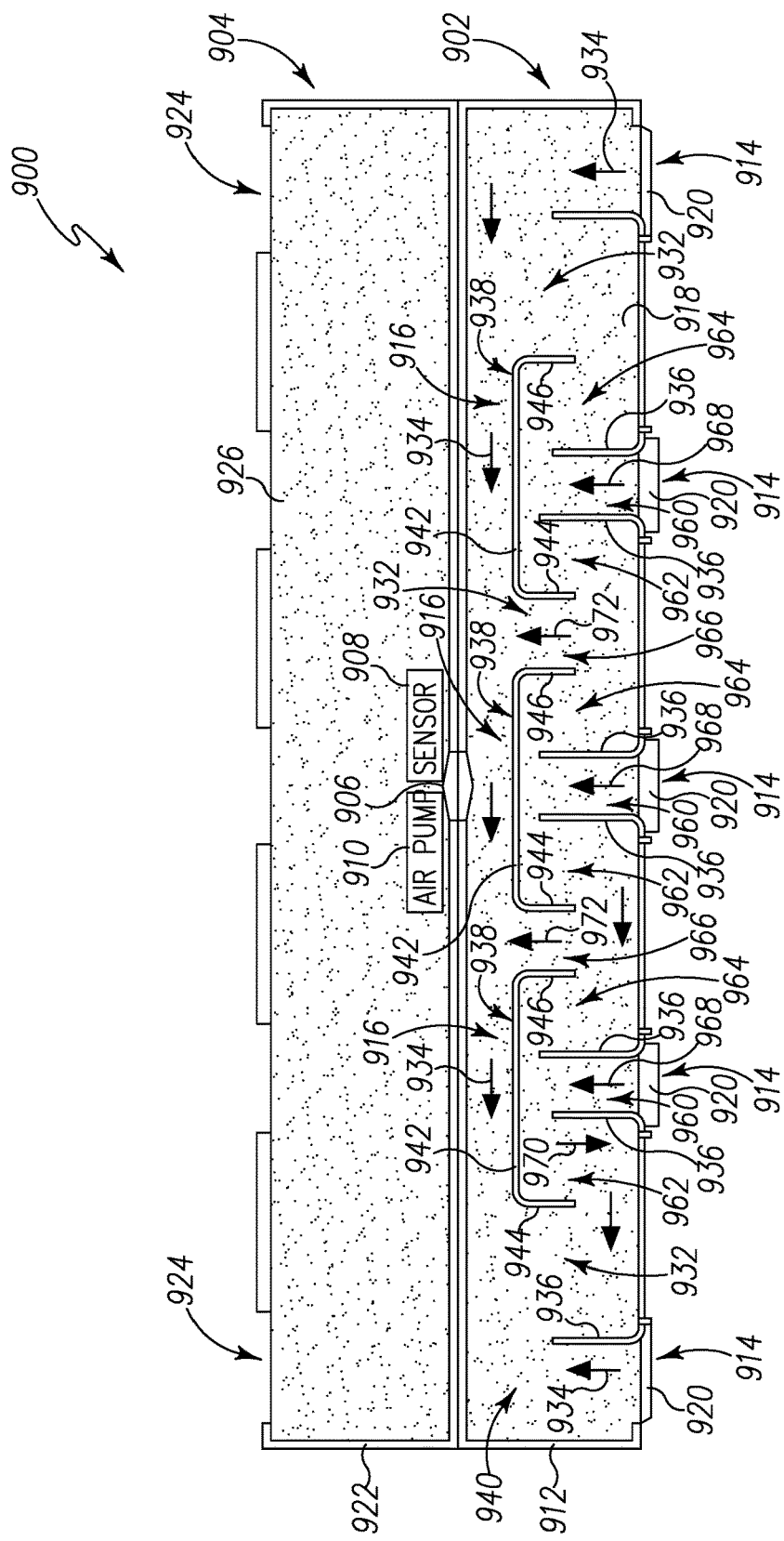
FIG. 10 is a top plan view of the pest control device of FIG. 9 in an open configuration.
Figure 11:
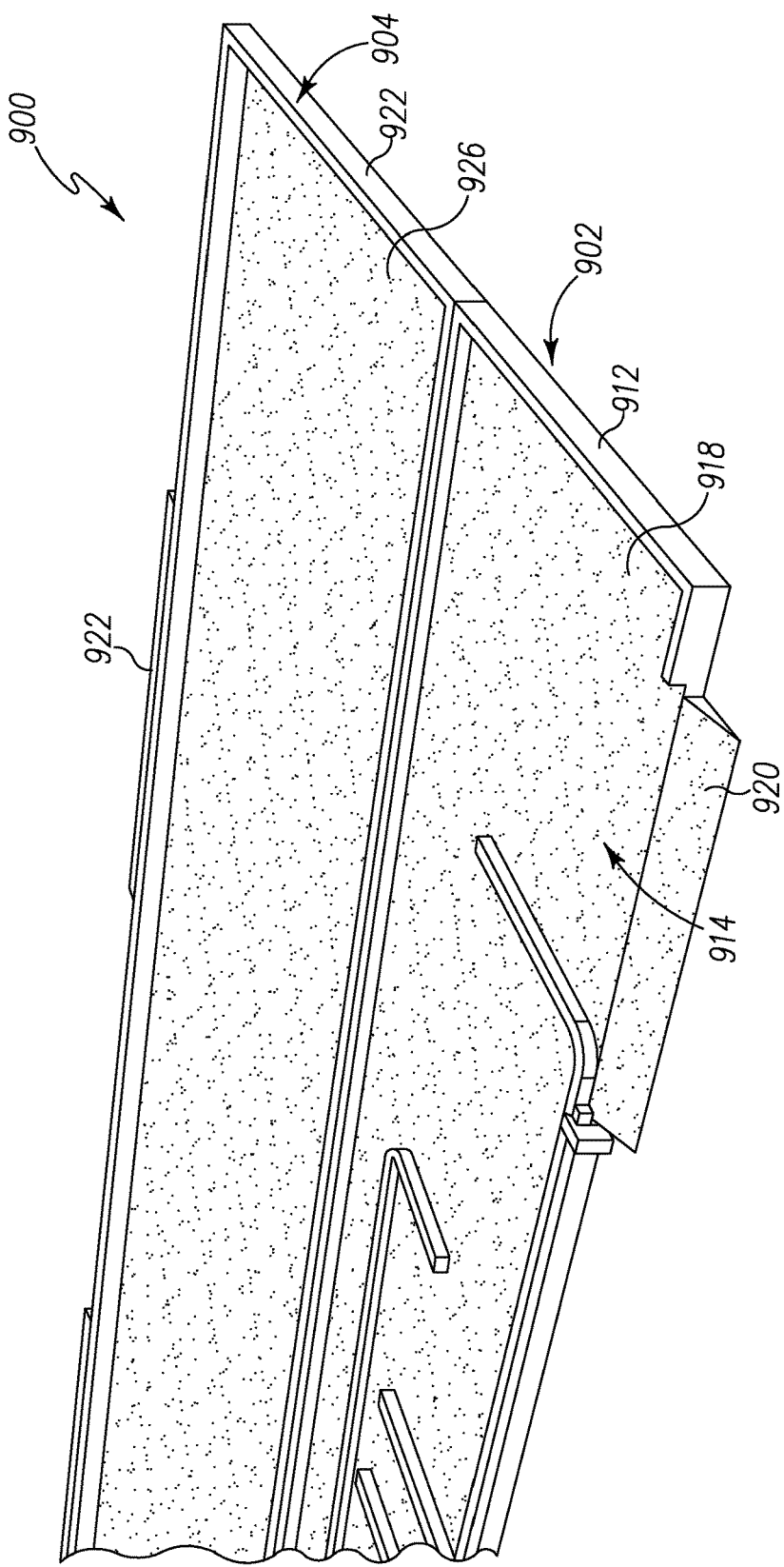
FIG. 11 is a perspective view of the pest control device of FIG. 9.

In the illustrative embodiment, the harborage device 900 is configured to be opened by a technician or other user to permit access to the chamber 940. Referring now to FIGS. 10 and 11, the harborage device 900 is shown in its open configuration. The harborage device 900 includes a bottom panel 902 and a top panel 904 that is pivotably coupled to the bottom panel 902 via a hinge 906. The hinge 906 allows the top panel 904 to move relative to the bottom panel 902 to permit access to the inner chamber 940. In use, the harborage device 900 is folded via the hinge 906 such that the top panel 904 is positioned on top of the bottom panel 902 to close the harborage device 900 (see FIGS. 9 and 12-13). It should be appreciated that, in some embodiments, the bottom panel 902 may be coupled to the top panel 904 via other types of fastener that permit the panels to be moved apart and permit access to the inner chamber 940.

Figure 12:
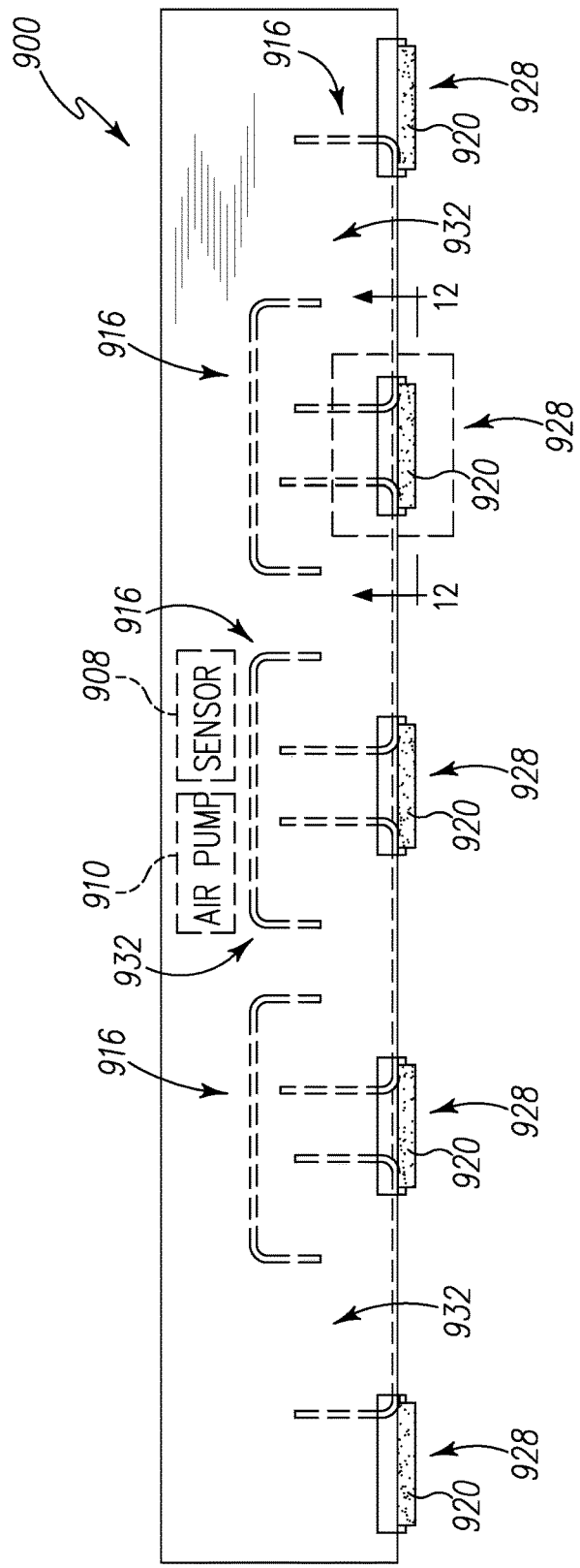
FIG. 12 is a top plan view of the pest control device of FIG. 9 in a closed position.

As shown in FIG. 10, the bottom panel 902 includes an outer frame 912 and a plurality of openings 914 disposed in the outer frame 912. The top panel 904 also includes an outer frame 922 that cooperates with the outer frame 912 of the bottom panel 902 to define the inner chamber 940. The top panel 904 also includes a plurality of openings 924 disposed in its outer frame 922 that are configured to align with the corresponding openings 914 of the bottom panel 902 to define the inlets 928 of the harborage device 900 when the harborage device 900 is closed (i.e., when the top panel 904 is folded on the bottom panel 902 via the hinge 906 as shown in FIGS. 11 and 12.)

The panels 902, 904 further include inner surfaces 918, 926, respectively. In the illustrative embodiment, the inner surfaces 918, 926 are coated with a textured material to attract pests into the harborage device 900. For example, the textured material may be a fibrous material. The textured material is configured to provide traction for pests to move inside of the harborage device 900 along the inner surfaces 918, 926. For example, the textured material may be woven (e.g. fabric) or non-woven (e.g. paper) and may be made of synthetic, natural, or blended fibers. In some embodiments, the textured material may be colored to attract pests. For example, to attract bed bugs, a paper with red-shade or black color may be used. It should be appreciated that the textured material is configured to provide minimal to no sorption of the targeted analyte to prevent or minimize any interference with the sensor detection. In some embodiments, a thickness of the texture material may be optimized to reduce the sorption of the targeted analyte.

Additionally, the bottom panel 902 further includes a plurality of inner walls 916 extending from the inner surface 918. As described in detail below, the plurality of inner walls 916 divide the inner chamber 940 into a plurality of channels 932. Each channel 932 is sized to receive one or more pests and configured to direct airflow from the inlets 928 toward the sensor 908 as indicated by arrows 934. It should be appreciated that, in some embodiments, the flow channels 932 may taper toward peripheries of the harborage device 900. Such tapered flow channels 932 are adapted to increase concentration of the targeted analyte in the harborage device 900 by restricting diffusion of the targeted analyte to narrower flow channels 932 and reduce losses of the targeted analyte to air space surrounding the pests.

The plurality of inner walls 916 include a plurality of guide walls 936 and a plurality of barrier walls 938. Each guide wall 936 is positioned on each side of an inlet 928 and extends in a first direction as shown by arrow 968. Each pair of guide walls 936 defines an inlet channel 960 of the plurality of channels 932. Each barrier wall 938 is spaced apart from the ends of the guide walls 936 and includes a first wall section 942, a second wall section 944 extending from an end of the first wall section 942, and a third wall section 946 extending from an opposite end of the first wall section 942 to form a generally U-shaped barrier.

The first wall section 942 is configured to extend in the second direction orthogonal to the first direction, while the second wall section 944 and the third wall section 946 extend parallel to the guide walls 936. It should be appreciated that the second wall section 944 cooperates with the guide wall 936 to define a first side channel 962 of the plurality of channels 932, while the third wall section 946 cooperates with the guide wall 936 to define a second side channel 964 of the plurality of channels 932. As described above, the plurality of channels 932 cooperate to define a flow path in the inner chamber 940 from the inlets 928 toward the sensor 908 as indicated by the arrows 934. To do so, the first channel 960 is configured to direct the airflow in the first direction from the corresponding inlet 928 and the first and second side channels 962, 964 are configured to direct the airflow in a third direction opposite the first direction as shown in arrow 970. Additionally, a fourth channel 966 is defined between the barrier walls 938, specifically between a third wall section 946 of one barrier wall 938 and a second wall section 944 of another barrier wall 938, to direct airflow in the first direction as shown in arrow 972. As can be seen in FIG. 10, the fourth channel 966 is offset from the inlets 928 of the harborage device 900.

As further shown in FIG. 10, the harborage device 900 includes the sensor 908 and an airflow device 910 to draw airflow toward the sensor 908 via the flow path. In the illustrative embodiment, the airflow device 910 is an air pump, such as, for example, a peristaltic or diaphragm pump. However, it should be appreciated that, in some embodiments, the airflow device 910 may be embodied as a compressor, a Micro-Electro-Mechanical-Systems (MEMS) device, or a fan. The sensor 908 and the air pump 910 are disposed in the top panel 904 of the harborage device 900 such that the sensor 908 and the air pump 910 are positioned in the inner chamber 940 of the harborage device 900. The sensor 908 and the air pump 910 are positioned on the inner surface 926 of the top panel 904 such that, when the harborage device 900 is closed, the sensor 908 and the air pump 910 do not engage the plurality of the inner walls 916, thereby avoiding interference with the airflow and/or the pest ability to move in the inner chamber 940. In the illustrative embodiment, the air pump 910 is positioned between the outer frame 922 and the sensor 908 in order to draw air from the inlets 928 toward and through the sensor 908. It should be appreciated that, in some embodiments, the air pump 910 may be omitted from the harborage device 900. In such embodiments, the sensor 908 may rely on the natural airflow within the inner chamber 940 to deliver the targeted analyte secreted by the pests to the sensor 908 for detection.

In some embodiments, the sensor 908 may include a barrier sheet that covers the sensor 908. The barrier sheet is made of a mesh material to prevent pests from coming in direct contact with the sensor 908. It should be appreciated that the mesh material does not block diffusion of the targeted analyte.

As described above, the sensor 908 is configured to detect the presence of pests. For example, in the illustrative embodiment, the sensor 908 is embodied as a resonator sensor such as a quartz crystal microbalance (QCM) or a small-scale QCM sensor. As described in detail above, the resonator sensor 908 is configured to detect the presence of pests by detecting a presence of a targeted biochemical analyte secreted by pests in air. It should be appreciated that, in some embodiments, the sensor 908 may be embodied as a cantilever sensor to detect a presence of pests as described in detail above. It should also be appreciated that the sensor 908 may be any sensor described above in regard to FIGS. 1-8.

In some embodiments, the sensor 908 may be positioned outside of the harborage device 900. In such embodiments, the sensor 908 is coupled to the harborage device 900 via a conduit, which is adapted to direct airflow from the harborage device 900 and feed air into the sensor 908 for detection. In some embodiments, an end of the conduit may be inserted up to 15 cm deep into the inner chamber 940 to create a draft-free environment in the inner chamber 930 to attract pests that avoid drafty locations (e.g., bed bugs). In some embodiments, the conduit may be inserted along one of the edges of the inner chamber 930. In other embodiments, the conduit may be oriented at an angle up to 90 degrees relative to one of edges of the harborage device 900.

It should be appreciated that, in some embodiments, the harborage device 900 may include a heating element to adjust the temperature in the inner chamber 940. In such embodiments, the harborage device 900 may also include a controller to operate the heating element and maintain the temperature in the inner chamber 940 above ambient temperature up to 40° C. to create a favorable condition for the bed bugs. Additionally, in some embodiments, the controller may further increase the temperature to about 100° C. to exterminate any pests detected in the inner chamber 940. In such embodiments, the controller may increase the temperature from the inlets 928 of the harborage device 900 toward the barrier wall 938 to about 100° C. in order to prevent the bed bugs within the inner chamber 940 from leaving the harborage device 900.

In some embodiments, the harborage device 900 may further include a pre-concentrator that accumulates the targeted analyte and releases the accumulated targeted analyte for pest detection. The pre-concentrator may be embodied as one or more sheets that sorb targeted biochemical analyte that covers at least a portion of the inner surfaces 918, 926 of the harborage device 900 (e.g., one or more pathways from the inlets 928 to the sensor 908). For example, the one or more sheets may be made of an analyte-sorbing material or a woven or non-woven fibrous material. In some embodiments, the one or more fibrous sheets may contain sorbent powder between fibers of a sheet of fibrous material or between two sheets of a fibrous material for higher sorption. It should be appreciated that the pre-concentrator may be configured to sorb and accumulate the targeted analyte for a period of time and then release the accumulated targeted analyte all at once when heated to provide more concentrated targeted analyte for sensor detection. This reduces the diffusion of the targeted analyte to air space surrounding the pests and may allow the sensor 908 to detect the presence of fewer pests.

For example, the pre-concentrator may be configured to absorb the targeted analyte at a first temperature and release the absorbed targeted analyte at a second temperature. For example, in some embodiments, the pre-concentrator may be a fibrous material such as, for example, paper, which is filled with sorbent powder, and is positioned on at least one of the inner surfaces 918, 926. In such embodiments, the pre-concentrator has a sorption phase and a desorption (i.e., release) phase. During the sorption phase, the heating element may be operated to increase the temperature inside of the harborage device 900 to above ambient temperature to attract pests, and the pre-concentrator is configured to absorb the targeted analyte secreted by the pests. During the desorption or release phase, the heating element is operated to further increase the temperature inside of the harborage device 900, and the targeted analyte is desorbed or released from the pre-concentrator. The desorption of the targeted analyte increases the concentration of the targeted analyte drawn by the air pump 910 into the sensor 908 for pest detection. It should be appreciated that the sensor 908 may detect the presence of pests continuously or intermittently during the desorption phase.

In some embodiments, the pre-concentrator may be embodied as a tube or a column that extends from the inlet 928 of the harborage device 900 to the sensor 908. In such embodiments, the tube is made of an analyte-sorbing material configured to sorb the targeted biochemical analyte as air surrounding the harborage device 900 passes through the tube. Upon heating the tube, the collected analytes in the tube are rapidly desorbed. It should be appreciated that the air pump 910 may facilitate to draw desorbed targeted analyte released from the pre-concentrator to the sensor 908 for detection.

In some embodiments, the harborage device 900 may include multiple heating elements. The heating elements may be uniformly distributed along the flow path to propagate heat pulses from the inlets 928 toward the sensor 908. For example, the heating elements may be activated in an order, from a heating element farthest from the sensor 908 to a heating element closed to the sensor 908 or vise versa, to desorb the targeted analyte from the pre-concentrator in a sequence. Subsequently, the air pump 910 may be activated to pull air into the sensor 908. When the fresh air is pulled in from the outside of the inner chamber 940 through the inlets 928 toward the sensor 908, air collects the targeted analyte desorbed from the pre-concentrator in the inner chamber 940 and carries into the sensor 908 providing a higher concentration of the targeted analyte for pest detection.

It should be appreciated that the pre-concentrator may be lined along the peripheries of the harborage device 900. In some embodiments, the pre-concentrator may be disposed adjacent to the sensor 908 opposite the air pump 910 such that the sensor 908 is positioned between the air pump 910 and the pre-concentrator. Such configuration allows the air pump 910 to draw desorbed targeted analyte released from the pre-concentrator to the sensor 908 for detection. In some embodiments, the sensor 908 may include an internal pre-concentrator. In some embodiments, the external pre-concentrator may be embodied as a test chamber sized to receive an amount of the targeted analyte.

In some embodiments, a barrier may be positioned between the outer frame 912 of the bottom panel 902 and the outer frame 922 of the top panel 904 when the harborage device 900 is in the closed configuration to prevent targeted analyte from diffusing out of the harborage device 900. For example, the barrier may be embodied as a lining between the outer frames 912, 922 may be made of an aluminized film. Such barrier may increase a concentration of the targeted analyte in the harborage device 900 for the sensor detection. The barrier may further provide a preferable condition by establishing a draft-free zone inside the harborage device 900 to attract pests that avoid drafty locations (e.g., bed bugs).

Figure 13:
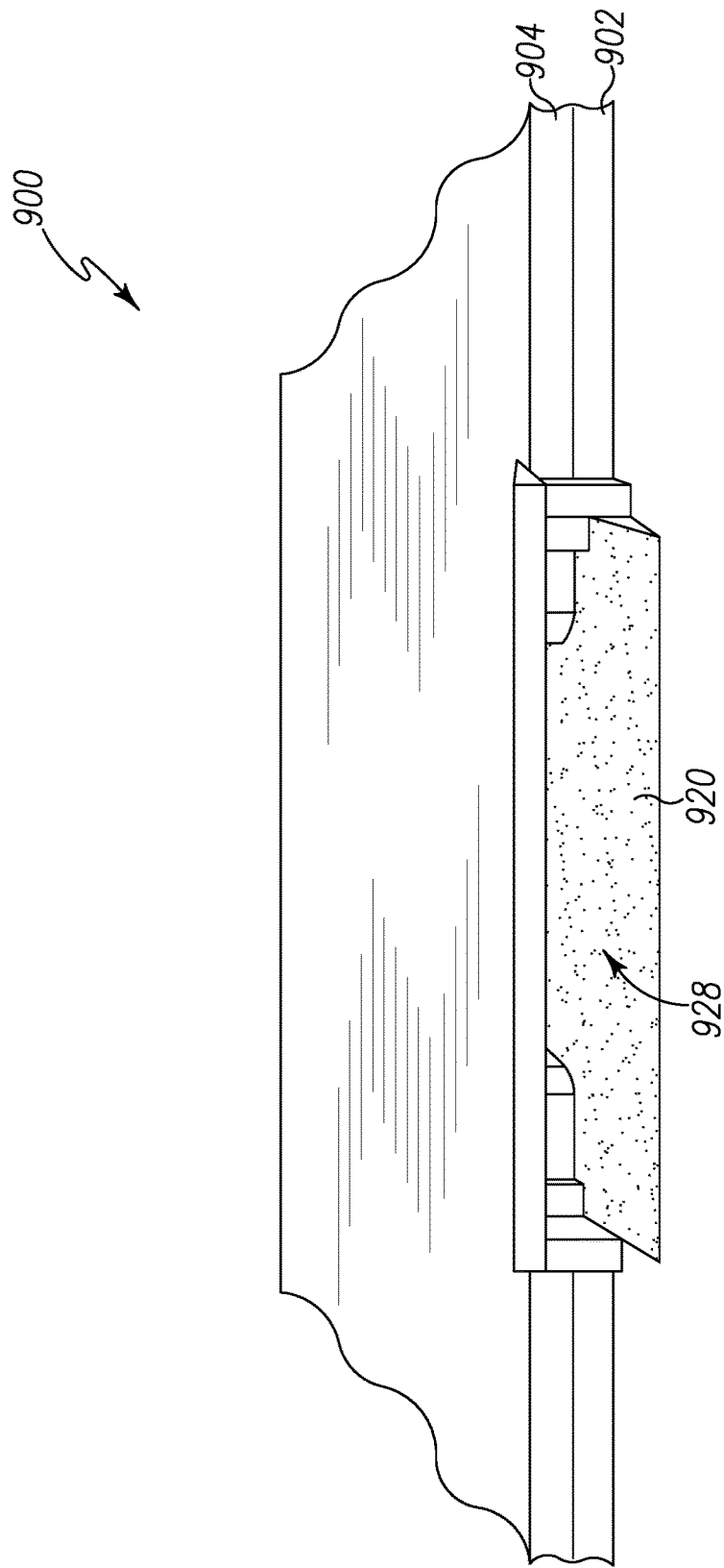
FIG. 13 is a perspective view of an inlet opening of the pest control device of FIG. 9.

Referring now to FIGS. 12 and 13, in use, the harborage device 900 is folded such that the outer frame 922 of the top panel 904 is positioned on top of the outer frame 912 of the bottom panel 902. As discussed above, when the harborage device 900 is in the closed configuration, the inner surface 918 of the bottom panel 902 faces but spaced apart from the inner surface 926 of the top panel 904 defining the inner chamber 940, which is configured to allow the pests to move in the inner chamber 940. In the illustrative embodiment, the width of inner chamber 940 (i.e., the distance between the inner surface 918 of the bottom panel 902 and the inner surface 926 of the top panel 904) becomes smaller toward the sensor 908 to create a narrower flow path near the sensor 908 to increase the concentration of the targeted analyte near the sensor 908 by restricting the diffusion of the targeted analyte to the narrow path. However, it should be appreciated that, in some embodiments, the width of the inner chamber 940 may be consistent throughout the harborage device 900.

As shown in FIG. 13, the bottom panel 902 further includes a plurality of ramp surfaces 920, each of which is positioned outside of each inlet 928 to guide pests into the corresponding inlet 928. In the illustrative embodiment, a width of each ramp surface 920 may range from 3 mm to 100 mm to correspond to the width of each inlet 928. In some embodiments, the bottom panel 902 may include one ramp surface 902 that extends along an entire width of the bottom panel 902.

As shown in FIG. 9, in the illustrative embodiment, the harborage device 900 is adapted to be positioned or secured to a bed headboard 952 of a bed 950 such that the bottom panel 902 is positioned between the surface of the bed headboard 952 and the top panel 904. When the harborage device 900 is secured to the bed headboard, each ramp surface 920 is configured to bridge between the surface of the bed headboard 952 and each inlet 928 such that the pests may travel from the bed into the harborage device 900. It should be appreciated that the ramp surface 920 may be coated with a textured material similar to the material on the inner surface 918 of the bottom panel 902 to provide pests traction to move upwardly along the ramp surface 920 into the harborage device 900. In some embodiments, the ramp surface 920 may be colored to create a favorable condition to attract pests into the harborage device 900.

In the illustrative embodiment, the harborage device 900 has a rectangular shape; however, it should be appreciated that the harborage device 900 may be in a polygon, a polygon with rounded corners, an oval, or a circle. It should be appreciated that external surfaces of the harborage device 900 may be in attractive color to attract pests. For example, the external surfaces of the harborage device 900 may be in red-shade or black color to attract bed bugs. It should also be appreciated that, in some embodiments, both bottom and top panels 902, 904 may be flat or curved to define the inner chamber 930 of harborage device 900. In other embodiments, one of the panels may be flat and the other panel is curved to reduce the material used.

In the illustrative embodiment, the harborage device 900 further includes a local indicator. The local indicator is coupled to the sensor 908 via a wire and is positioned on the outer surface of the top panel 904 of the harborage device 900. However, in some embodiments, the local indicator may be positioned outside of the harborage device 900 via a wire. In other embodiments, the local indicator may be wirelessly connected to the sensor 908 harborage device 900. Similar to the local indicator 218 discussed in detail above, the local indicator may be embodied as any type of indicator that is capable of generating an alert to notify a human operator or a technician. For example, the local indicator of the harborage device 900 may be embodied as a visual and/or audible indicator. In some embodiments, the visual indicator may include a light emitting diode (LED), fluorescent, incandescent, and/or neon type light source. The audible indicator may generate an alert sound to notify the technician. In the illustrative embodiment, the local indicator generates an alert indicative of a presence or absence of bed bugs. For example, in some embodiments, the LED light indicator may be energized to project a colored light, change color, or change from a non-blinking light to a blinking light to indicate the presence of bed bugs. In other embodiments, the audible local indicator may generate sound to indicate the presence of bed bugs.

In other embodiments, the harborage device 900 may include a wireless communication circuit to communicate with a pest control system or server to notify when pests are detected and/or the sensor requires maintenance. As described in detail above, the wireless communication circuit may be configured to use any one or more communication technologies (e.g., wireless or wired communications) and associated protocols (e.g., Ethernet, Bluetooth®, Wi-Fi®, WiMAX, LTE, 5G, etc.) to effect such communication.

In use, a human operator or a technician may mount the harborage device 900 on the bed headboard 952 of the bed 950 to detect the presence of the pests that have a preferred habitat near beds or mattresses, for example, bed bugs. The harborage device 900 is oriented such that the bottom panel 902 of the harborage device 900 is positioned on the surface of the bed headboard 952. This allows the ramp surfaces 920 of the harborage device 900 to bridge between the surface of the bed headboard 952 and the inlets 928 to allow the pests to travel from the bed headboard 952 into the inner chamber 930 of the harborage device 900. As discussed above, the ramp surface 920 may be colored or coated with a textured material to create a favorable condition to attract the targeted pests along the ramp surface 902 into the inner chamber 930.

The air pump 910 of the harborage device 900 is continuously or periodically activated to pull air from the inlets 928 to draw the targeted biochemical analyte from area surrounding the pests in the inner chamber 930 toward the sensor 908. When air is pulled into the sensor 908, the sensor 908 is configured to detect the targeted biochemical analyte in air to detect the presence of the pests. For example, the sensor 908 is configured to detect the targeted biochemical analyte, such as T2H, T2O, 4-oxo-(E)-2-hexenal, and/or 4-oxo-(E)-2-octenal, to detect the presence of bed bugs in or near the harborage device 900. The sensor 908 then transmits a signal to the local indicator to generate an alert to notify the human operator or the technician of the presence of bed bugs.

As described above, the harborage device 900 may not include any airflow devices, including, for example, an air pump 910. Without an air pump 910 pulling air towards the sensor 908, the sensor 908 relies on the targeted analyte present in the air surrounding the pests to reach the sensor 908 primarily via diffusion through air within the inner chamber 940. In other words, the targeted biochemical analyte molecules spread away from the source (i.e., analyte-emitting bed bugs) in all available directions through air in the inner chamber 930 of the harborage device 900. In such embodiments, the location of the sensor 908 in the inner chamber 940 may be selected to minimize the maximum diffusion path (e.g., an open passageway from the inlet 928 to the sensor 908). The harborage device may further include an impermeable liner (e.g., aluminized film) positioned in a gap between the outer frames 912, 922 of the top and bottom panels 902, 904, respectively, to minimize the loss of the targeted analyte through the gap to maximize the concentration of the targeted analyte in the inner chamber 940 for the sensor detection. It should be appreciated that, in such embodiments, the harborage device may further include a pre-concentrator similar to the pre-concentrator described in detail above. In other embodiments, the harborage device may also include one or more heating elements similar to the heating element described in detail above.

Figure 14:
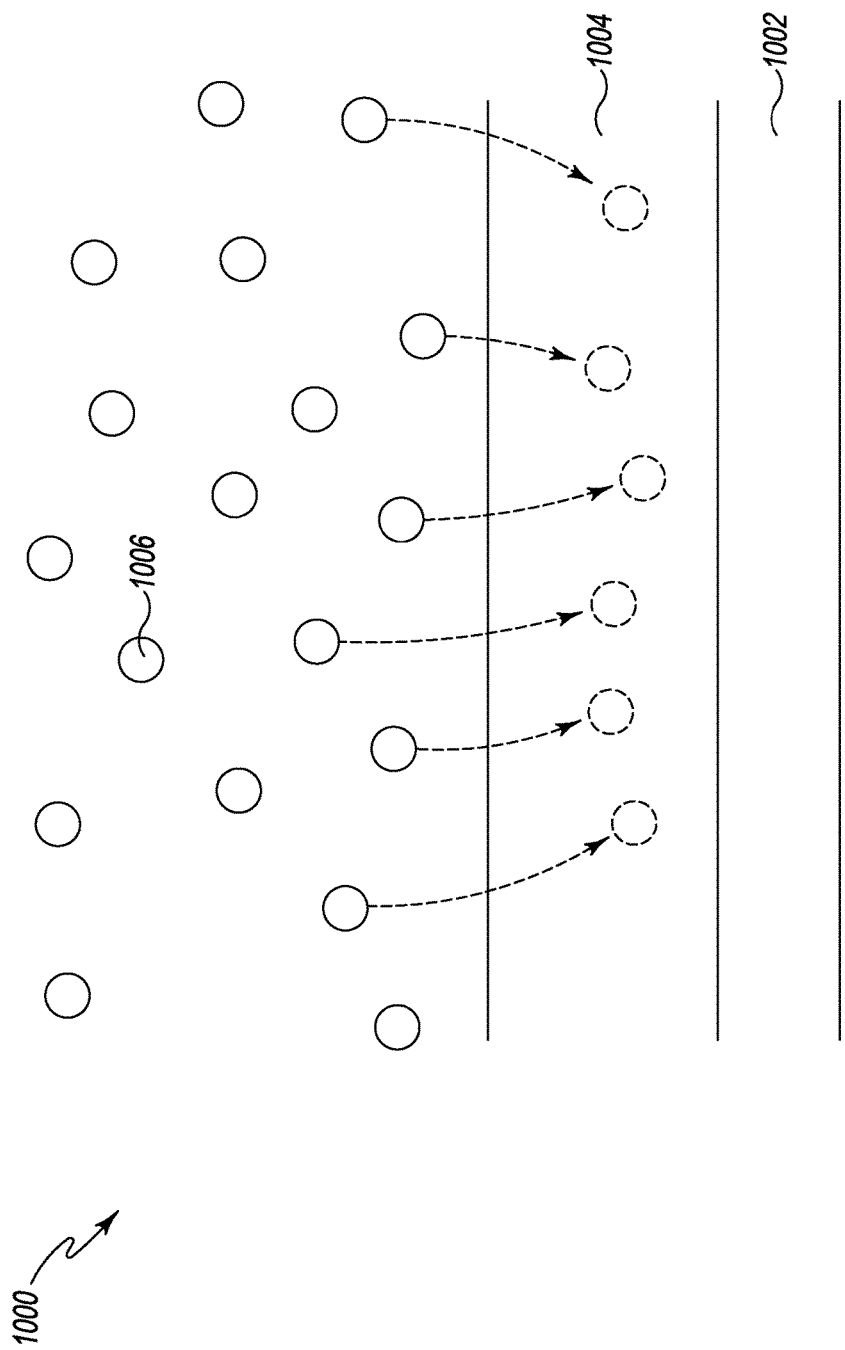
FIG. 14 is a cross-sectional view of at least one embodiment of a detection sensor of a pest control device that includes a sensor cell and a sensor coating coated on the surface of the sensor cell, wherein the sensor coating includes a coating gel compound made of a polymer gel and an agent that detects an analyte found in secretion bed bugs.

Referring now to FIG. 14, another embodiment of a sensor 1000 is shown. Similar to the sensor 210, the sensor 1000 includes a sensor cell 1002 (e.g., a quartz crystal resonator) and a sensor coating 1004 coated on the surface of the sensor cell 1002. In the illustrative embodiment, the sensor coating 1004 includes a coating gel compound made of a polymer gel and the agent (e.g., dioctyl-CTI). As discussed above, the agent is configured to react with the targeted biochemical analyte 1006 found in the secretion of bed bugs (e.g., T2H, T2O, 4-oxo-(E)-2-hexenal, or 4-oxo-(E)-2-octenal).

In the illustrative embodiment, the polymer gel has high viscosity (e.g., a jelly-like consistency), optionally exhibits viscoplastic properties (e.g., yield stress), and high thermal and chemical stability to form a stable coating on the surface of the sensor 1002. As such, rather than directly coating the agent onto the surface of the sensor 1002, the polymer gel is adapted to form a medium to immobilize the agent on top of the surface of the sensor 1002. Additionally, in the illustrative embodiment, a polymer gel that has a relatively low molecular weight was used to achieve a desired viscosity level of the polymer gel and increase the detection sensitivity of the targeted biochemical analyte, which is discussed further below. It should be appreciated that liquid to be used to dissolve polymer to form the polymer gel depends on a type of polymer to achieve a stable interface that has high thermal and chemical stability. An exemplary polymer gel may include polymethylphenylsiloxiane (PMPS), polydimethylsiloxane (PDMS), fluoroalcohol polycarbosilane which is available from Seacoast Science, Inc. of Carlsbad, Calif. and marketed as the SC-F101, fluoroalcohol polysiloxane which is available from Seacoast Science, Inc. of Carlsbad, Calif. and marketed as SXFA, bisphenol-containing polymer (BSP3), poly-2-dimethyl-amin-ethyl-methacrylate (PDMAEMC), or polymers with silicone (Si) and flourine (F). It should be appreciated that, in some embodiments, the coating gel compound may include more than one type of polymer gel.

In use, as shown in FIG. 14, the targeted biochemical analyte 1006, typically in a gaseous state, present in the air surrounding the sensor 1000 diffuses into the coating gel compound of the sensor coating 1004. The diffused targeted biochemical analyte 1006 then reacts with the agent present in the coating gel compound and produces an agent-targeted biochemical analyte product that has a higher molecular weight than the agent alone. In the illustrative embodiment, a low molecular weight polymer gel was used to form the coating gel compound, such that even a small weight change may be detected indicating a presence of a small amount of the targeted biochemical analyte 1006. It should be appreciated that the diffused targeted biochemical analyte 1006 that has yet to react with the agent may be released back to the air based on solubility of the coating gel compound.

In the illustrative embodiment, the sensor coating 1004 was formed by spin coating to deposit uniform films to the surface of the sensor cell 1002 using a spin coater. To form a thin uniform coating, a thick layer of the coating gel compound was deposited onto the sensor cell 1002 and the excess of the coating gel compound was removed via centrifugal force exerted by spinning using a spin coater. In some embodiments, spray coating may be used to form the sensor coating 1004 by spraying a dosed amount of a mist of the coating gel compound onto the sensor cell 1002. The mist may be produced by using an atomizing nozzle (e.g., piezoelectric or pressurized-gas-driven), an inkjet printing head (e.g., piezoelectric or thermal), or a similar device ejecting a single micro-drop of solution at a time. In other embodiments, the sensor coating 1004 may be formed by using a capillary deposition method, a soft lithography (e.g. microcontact printing), or a dip coating method. It should be appreciated that, in each of the embodiments, the coating gel compound may be diluted in a volatile solvent to control the viscosity of the coating gel compound during the coating process.

Figure 15:
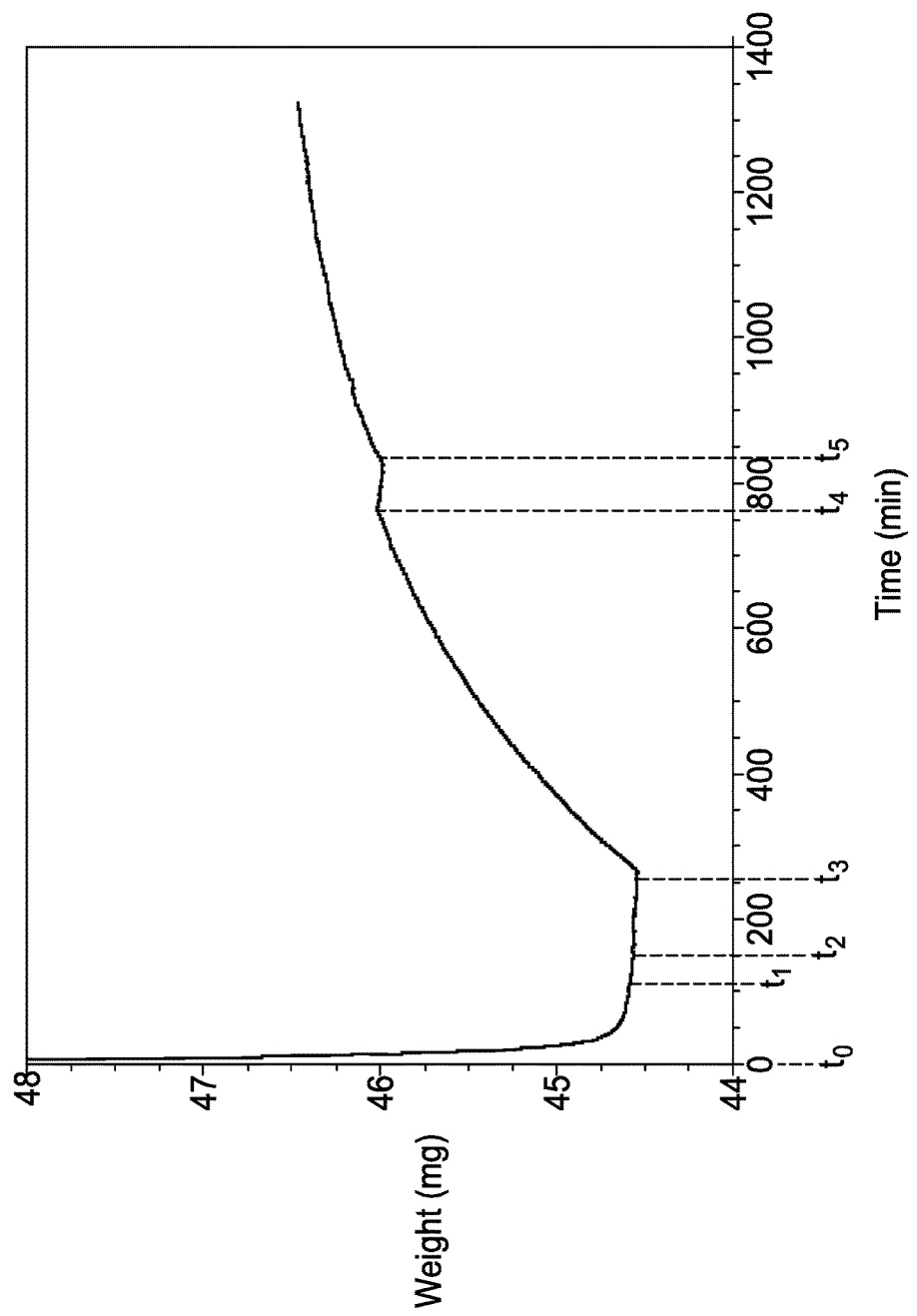
FIG. 15 is a graphical view that illustrates a mass change of polydimethylsiloxane (PDMS) coating gel compound caused by reactions between an agent in the PDMS coating gel compound and the targeted biochemical analyte present in the air surrounding the PDMS polymer gel.

Referring now to FIG. 15, a graph illustrates a mass change of a coating gel compound that includes polydimethylsiloxane (PDMS) polymer gel and CTI agent. As discussed above, the mass change is caused by the reactions between the CTI agent in the PDMS coating gel compound and trans-2-hexenal (T2H) (i.e., the targeted biochemical analyte) present in the air surrounding the PDMS coating gel compound. Prior to introducing the targeted biochemical analyte, the temperature was increased to about 50 degree Celsius between to and $t_1$ for about 110 minutes to ensure that the PDMS coating gel compound is clean. As discussed above, the reaction between the targeted biochemical analyte and the agent may be reversible with heat. By heating the PDMS coating gel compound at about 50 degree Celsius for about 110 minutes ensures that any possible targeted biochemical analyte reacted with the agent in the PDMS coating gel compound is removed from the PDMS coating gel compound. Additionally, any possible targeted biochemical analyte diffused in the PDMS coating gel compound that may not have reacted with the agent may also be released from the PDMS coating gel compound.

The temperature was dropped to about 35 degree Celsius at $t_2$ and was remained at about 35 degree Celsius. It should be noted that the weight of the PDMS coating gel compound remained relatively constant until the targeted biochemical analyte was introduced at $t_3$. In other words, in the absence of the targeted biochemical analyte, no significant weight change in the PDMS coating gel compound that includes PDMS polymer gel and CTI agent was detected.

At $t_3$, a sample with the targeted biochemical analyte was released into the air surrounding the PDMS coating gel compound until $t_4$. The targeted biochemical analyte in the air surrounding the PDMS coating gel compound is adapted to diffuse into the PDMS coating gel compound based on the solubility of the PDMS coating gel compound. Once the targeted biochemical analyte is diffused in the PDMS coating gel compound, the targeted biochemical analyte is configured to react with the targeted biochemical analyte in the PDMS coating gel compound and produce an agent-targeted biochemical analyte product that has a higher molecular weight than the agent alone. Accordingly, as can be seen in FIG. 15, the weight plot continuously increased during the release of the targeted biochemical analyte from $t_3$ to $t_4$ indicating an increase in weight of the PDMS coating gel compound.

When the flow of the sample was stopped at $t_4$, the weight of the PDMS coating gel compound slightly decreased. Such decrease in the weight may be caused by a release of unreacted targeted biochemical analyte from the PDMS coating gel compound. For example, the targeted biochemical analyte in the air surrounding the sensor 1000 may have diffused in the PDMS coating gel compound during $t_3$ and $t_4$ but has not yet to react with the agent in the PDMS coating gel compound. Such unreacted targeted biochemical analyte is adapted to diffuse out of the PDMS coating gel compound back to the surrounding air. Additionally, in some embodiments, the reaction between the agent and the targeted biochemical analyte may be reversible. In such embodiments, in the absence of the targeted biochemical analyte in the surrounding, the agent-targeted biochemical analyte products may be reversed back to the reactants (i.e., the agent and the targeted biochemical analyte) over time.

At $t_5$, the sample with the targeted biochemical analyte was reintroduced to the air surrounding the sensor 1000 and the weight of the PDMS coating gel compound continued to increase again from the reaction between the targeted biochemical analyte of the sample and the agent in the PDMS coating gel compound.

Figure 16:
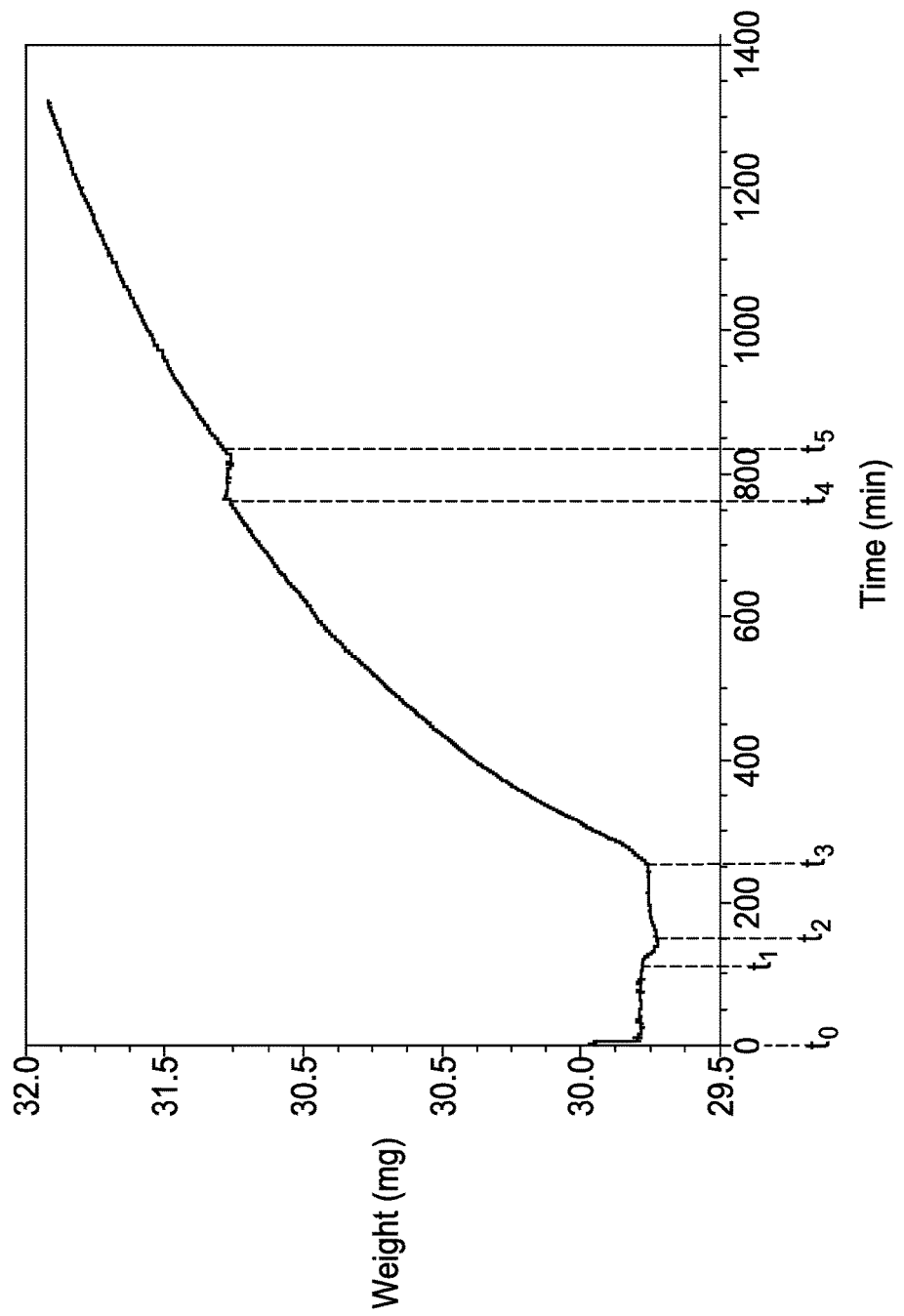
FIG. 16 is a graphical view that illustrates a mass change of polymethylphenylsiloxiane (PMPS) coating gel compound caused by reactions between an agent in the PMPS coating gel compound and the targeted biochemical analyte present in the air surrounding the PMPS polymer gel.

Referring now to FIG. 16, a graph illustrates a mass change of another coating gel compound that includes polymethylphenylsiloxiane (PMPS) polymer gel and CTI agent. Similar to FIG. 15, the mass change is caused by the reactions between the CTI agent in the PMPS coating gel compound and trans-2-hexenal (T2H) (i.e., the targeted biochemical analyte) present in the air surrounding the PMPS coating gel compound.

Prior to introducing the targeted biochemical analyte, the temperature was increased to about 50 degree Celsius between $t_0$ and $t_1$ for about 110 minutes to ensure that the PMPS coating gel compound is clean. As discussed above, the reaction between the targeted biochemical analyte and the agent may be reversible with heat. By heating the PMPS coating gel compound at about 50 degree Celsius for about 110 minutes ensures that any possible targeted biochemical analyte reacted with the agent in the PMPS coating gel compound is removed from the PMPS coating gel compound. Additionally, any possible targeted biochemical analyte diffused in the PMPS coating gel compound that may not have reacted with the agent may also be released from the PMPS coating gel compound.

The temperature was dropped to about 35 degree Celsius at $t_2$ and was remained at about 35 degree Celsius. It should be noted that the weight of the PMPS coating gel compound remained relatively constant until the targeted biochemical analyte was introduced at $t_3$. In other words, in the absence of the targeted biochemical analyte, no significant weight change in the PMPS coating gel compound that includes PMPS polymer gel and CTI agent was detected.

At $t_3$, a sample with the targeted biochemical analyte was released into the air surrounding the PMPS coating gel compound until $t_4$. The targeted biochemical analyte in the air surrounding the PMPS coating gel compound is adapted to diffuse into the PMPS coating gel compound based on the solubility of the PMPS coating gel compound. Once the targeted biochemical analyte is diffused in the PMPS coating gel compound, the targeted biochemical analyte is configured to react with the targeted biochemical analyte in the PMPS coating gel compound and produce an agent-targeted biochemical analyte product that has a higher molecular weight than the agent alone. Accordingly, as can be seen in FIG. 16, the weight plot continuously increased during the release of the targeted biochemical analyte from $t_3$ to $t_4$ indicating an increase in weight of the PMPS coating gel compound.

When the flow of the sample was stopped at $t_4$, the weight of the PMPS coating gel compound slightly decreased. As discussed above, such decrease in the weight may be caused by a release of unreacted targeted biochemical analyte from the PMPS coating gel compound. For example, the targeted biochemical analyte in the air surrounding the sensor 1000 may have diffused in the PMPS coating gel compound during $t_3$ and $t_4$ but has not yet to react with the agent in the PMPS coating gel compound. Such unreacted targeted biochemical analyte is adapted to diffuse out of the PMPS coating gel compound back to the surrounding air. Additionally, in some embodiments, the reaction between the agent and the targeted biochemical analyte may be reversible. In such embodiments, in the absence of the targeted biochemical analyte in the surrounding, the agent-targeted biochemical analyte products may be reversed back to the reactants (i.e., the agent and the targeted biochemical analyte) over time.

At $t_5$, the sample with the targeted biochemical analyte was reintroduced to the air surrounding the sensor 1000 and the weight of the PMPS coating gel compound continued to increase again from the reaction between the targeted biochemical analyte of the sample and the agent in the PMPS coating gel compound.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:
1. A pest control device comprising:
a sensor including a sensor cell, wherein a surface of a sensor cell is coated with an agent that reacts with a targeted biochemical analyte secreted by pests, and
a controller coupled to the sensor, the controller being configured to:
receive sensor data from the sensor cell indicative of a rate of change in sensor mass detected on the surface of the sensor cell, the rate of change correlating to an increase in the concentration of the targeted biochemical analyte,
determine whether the rate of change in the sensor mass based on the received sensor data exceeds a predefined threshold rate, and
transmit a pest detection alert notification to a server in response to a determination that the rate of change exceeds the predetermined threshold rate;
wherein the controller is further configured to:
activate a timer when the rate of change exceeds a predefined threshold rate,
deactivate the timer when the rate of change returns to less than the predefined threshold rate,
determine an amount of time that the rate of change in the sensor mass exceeded the predefined threshold rate, and
determine whether the amount of time is greater than a predefined time period,
wherein to transmit the pest detection alert notification comprises to transmit a pest detection alert notification in response to a determination that the amount of time is greater than the predefined time period.

2. The pest control device of claim 1 further comprising a handle providing a grip for a human operator to move the pest control device to identify a localized area of the targeted biochemical analyte.

3. The pest control device of claim 1, wherein the predefined threshold rate is a base mass change rate in the presence of bed bugs and the targeted biochemical analyte comprises an analyte found in secretion of bed bugs.

4. The pest control device of claim 1, wherein the agent comprises dioctyl cyclic thiol intermediate (dioctyl-CTI).

5. The pest control device of claim 1, wherein the agent comprises cyclic thiol intermediate (CTI).

6. The pest control device of claim 1, wherein the sensor is a quartz crystal microbalance and the sensor cell is a quartz crystal resonator.

7. The pest control device of claim 1, wherein the surface of the sensor cell is coated with a coating gel compound that includes a polymer gel and the agent.

8. A method of detecting a presence of pests comprising:
receiving data indicative of a sensor mass rate of change from a sensor,
determining whether the sensor mass rate of change exceeds a predefined threshold rate, and
transmitting a pest detection alert notification to a server in response to a determination that the rate of change exceeds the predetermined threshold rate,
wherein the sensor includes a coating that reacts with a targeted biochemical analyte secreted by pests, and the sensor mass rate of change correlates to an increase in a concentration of a targeted biochemical analyte;

activating a timer when the rate of change exceeds a predefined threshold rate, deactivating the timer when the rate of change returns to less than the predefined threshold rate, determining an amount of time that the rate of change in the sensor mass exceeded the predefined threshold rate, and determining whether the amount of time is greater than a predefined time period, wherein transmitting the pest detection alert notification comprises transmitting a pest detection alert notification in response to a determination that the amount of time is greater than the predefined time period.

9. The method of claim 8, wherein the predefined threshold rate is a base mass change rate in the presence of bed bugs.

10. The method of claim 8, wherein the coating comprises dioctyl cyclic thiol intermediate (dioctyl-CTI).

11. The method of claim 8, wherein the coating comprises cyclic thiol intermediate (CTI).

12. The method of claim 8, wherein the sensor is a quartz crystal microbalance.

13. The method of claim 8, wherein the coating is a coating gel compound that includes a polymer gel and the agent.

14. A method of detecting a presence of pests comprising:
receiving first sensor data from a sensor,
receiving second sensor data from the sensor,
determining a first slope of signal change based on the first and second sensor data, receiving third sensor data from the sensor, determining a second slope of signal change based on the second and third sensor data, determining if the second slope is different from the first slope, and transmitting a pest detection alert notification to a server in response to a determination that the second slope is different from the first slope, wherein the sensor includes a coating that reacts with a targeted biochemical analyte secreted by pests, and the signal change correlates to an increase in a concentration of a targeted biochemical analyte;

activating a timer when the second slope is different from the first slope, receiving sensor data from the sensor and determining a slope of signal change based on the sensor data while the timer is active, deactivating the timer upon detecting no change in slope, determining a time interval measured by the timer, and determining whether the time interval is greater than a predefined time period, wherein transmitting the pest detection alert notification comprises transmitting a pest detection alert notification in response to a determination that the time interval is greater than the predefined time period.

15. The method of claim 14, wherein the predefined threshold rate is a base mass change rate in the presence of bed bugs.

16. The method of claim 14, wherein the coating comprises dioctyl cyclic thiol intermediate (dioctyl-CTI) or cyclic thiol intermediate (CTI).

17. The method of claim 14, wherein the coating is a coating gel compound that includes a polymer gel and one of dioctyl cyclic thiol intermediate (dioctyl-CTI) or cyclic thiol intermediate (CTI).

\* \* \* \* \*